US012601659B2

(12) United States Patent
Miller et al.

(10) Patent No.: US 12,601,659 B2
(45) Date of Patent: Apr. 14, 2026

(54) SYSTEM, APPARATUS AND METHOD FOR LANDFILL GAS SENSING

(71) Applicant: THE REMEDIATION GROUP PTY LTD, Victoria (AU)

(72) Inventors: Jonathan Glen Miller, Victoria (AU); Daniel Shane Egan, Victoria (AU); Abbas Zahedi Kouzani, Victoria (AU); Scott Daryl Adams, Victoria (AU); Dean Michael Corva, Victoria (AU); Nathan Ian Semianiw, Victoria (AU); Tianhao Wu, Victoria (AU); Matthew Zampatti, Victoria (AU)

(73) Assignee: THE REMEDIATION GROUP PTY LTD., Victoria (AU)

( * ) Notice: Subject to any disclaimer, the term of this patent is extended or adjusted under 35 U.S.C. 154(b) by 296 days.

(21) Appl. No.: 18/278,109

(22) PCT Filed: Feb. 22, 2022

(86) PCT No.: PCT/AU2022/050134
§ 371 (c)(1),
(2) Date: Aug. 21, 2023

(87) PCT Pub. No.: WO2022/178574
PCT Pub. Date: Sep. 1, 2022

(65) Prior Publication Data
US 2024/0142351 A1 May 2, 2024

(30) Foreign Application Priority Data
Feb. 23, 2021 (AU) ................................. 2021900475

(51) Int. Cl.
G01N 1/22 (2006.01)
G01N 33/00 (2006.01)

(52) U.S. Cl.
CPC ......... G01N 1/2247 (2013.01); G01N 1/2273 (2013.01); G01N 1/2294 (2013.01);
(Continued)

(58) Field of Classification Search
CPC .. G01N 1/2247; G01N 1/2273; G01N 1/2294; G01N 33/0062; G01N 33/0004; G01N 33/497; G01N 7/14; G01N 33/4977
See application file for complete search history.

(56) References Cited

U.S. PATENT DOCUMENTS

2001/0005812 A1    6/2001  Brookshire et al.
2016/0238494 A1*   8/2016  Chrin, II ............ G01N 33/0073
(Continued)

OTHER PUBLICATIONS

Notification of Transmittal of the International Search Report and Written Opinion issued by the Australian Patent Office dated Apr. 19, 2022, for PCT/AU2022/050134 (18 pages).

*Primary Examiner* — David Z Huang
(74) *Attorney, Agent, or Firm* — Ballard Spahr LLP

(57) ABSTRACT

An apparatus including: a housing configured for installation in a landfill; a differential pressure sensor and at least one gas sensor in the housing; and a first valve configured to control landfill gas (LFG) flow to the at least one gas sensor, wherein the first valve is configured to open when the differential pressure sensor detects a selected pressure difference or pressure difference change between the atmospheric air pressure and the LFG pressure.

16 Claims, 22 Drawing Sheets

(52) U.S. Cl.
    CPC ....... *G01N 33/0062* (2013.01); *G01N 33/004*
                (2013.01); *G01N 33/0052* (2013.01)

(56) References Cited

U.S. PATENT DOCUMENTS

| 2017/0254787 | A1* | 9/2017 | Campanella | ....... | G01N 33/0036 |
| 2019/0070646 | A1 | 3/2019 | Elkins | | |
| 2020/0101505 | A1* | 4/2020 | Quigley | .................... | B09B 1/00 |

* cited by examiner

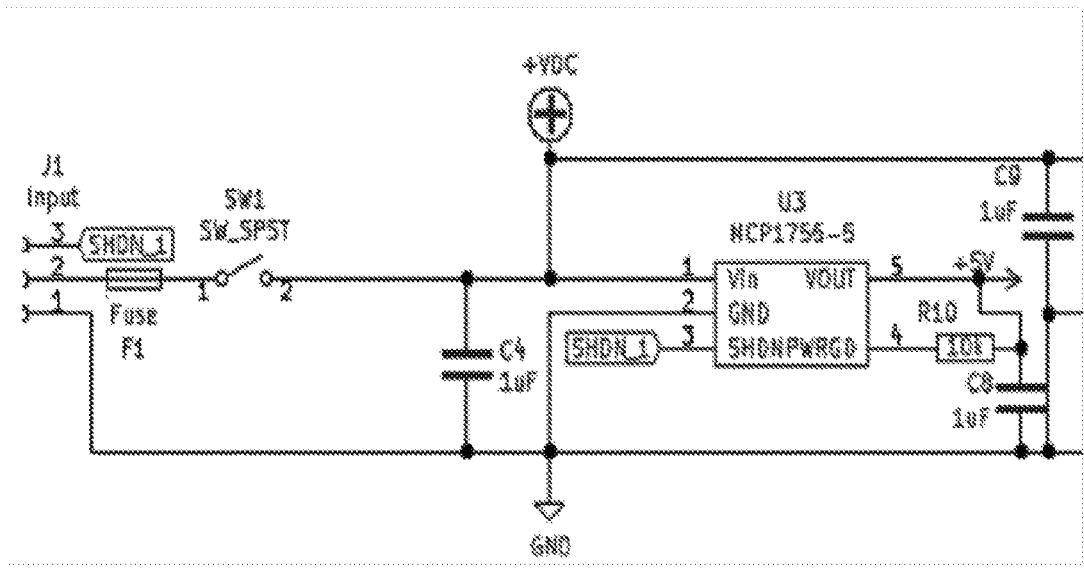
FIG. 17A
FIG. 17B
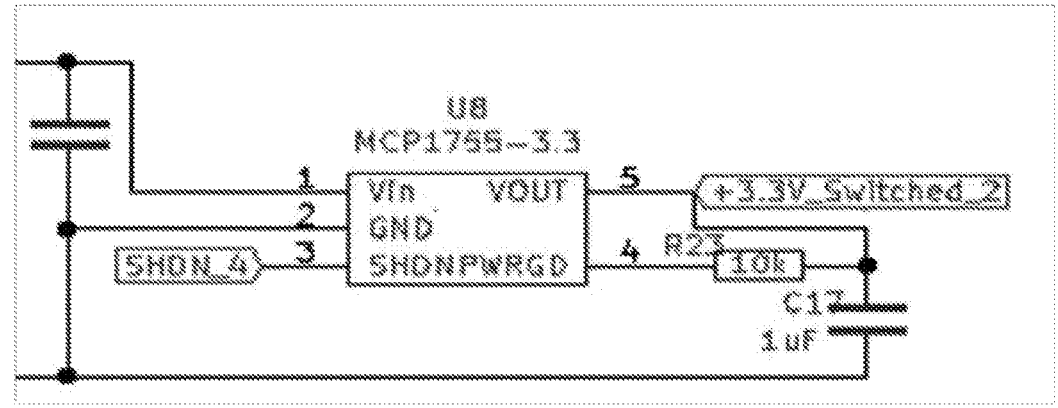
FIG. 17C

230

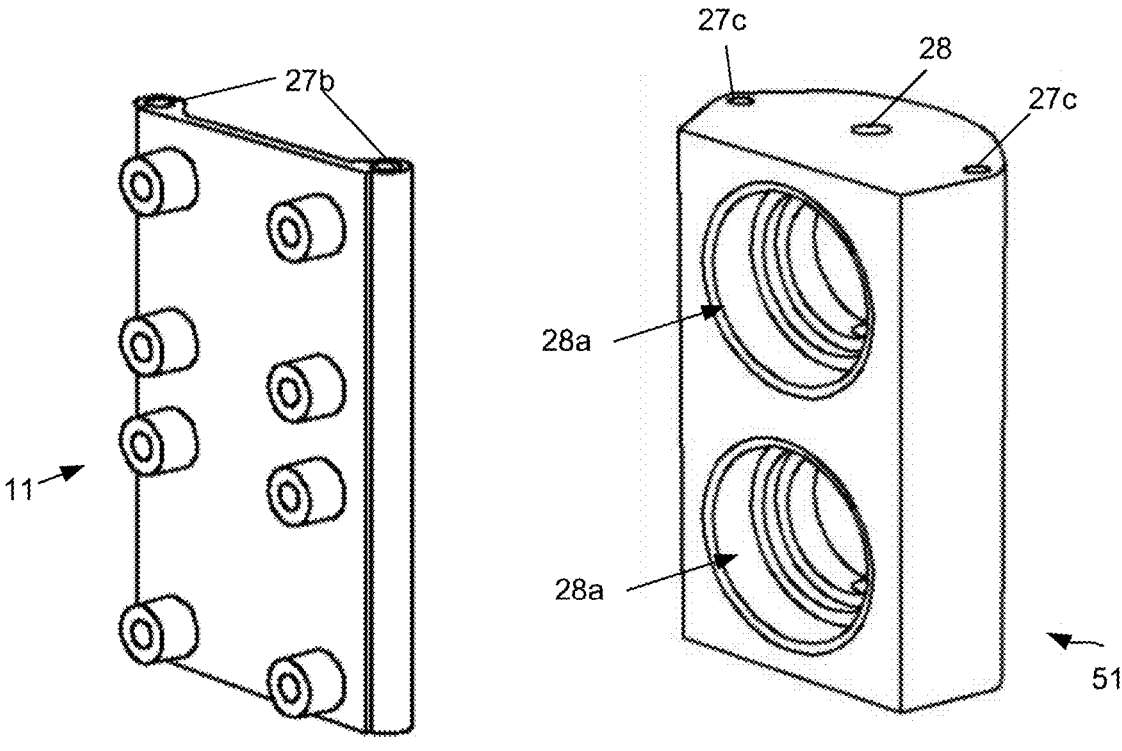
FIG. 27A                    FIG. 27B
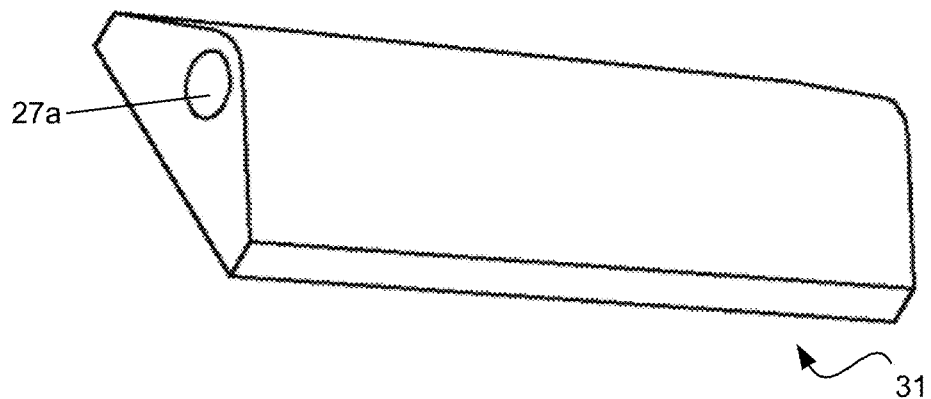
FIG. 27C

SYSTEM, APPARATUS AND METHOD FOR LANDFILL GAS SENSING

CROSS-REFERENCE TO RELATED APPLICATIONS

The present application is a national phase filing under 35 U.S.C. § 371 of International Application No. PCT/AU2022/050134, filed on Feb. 22, 2022, which claims the benefit of AU patent application No. 2021900475, filed Feb. 23, 2021. The contents of these earlier filed applications are hereby incorporated herein by reference in their entirety.

TECHNICAL FIELD

The present disclosure relates to a system, an apparatus and a method for landfill gas (LFG) sensing.

BACKGROUND

Due to natural decomposition, landfills generate landfill gas (LFG), which can be toxic. LFG is generated by the degradation of organic material in waste that is deposited into landfills. The age and composition of waste, along with a number of environmental factors, can influence the production of LFG. LFG can present a number of different risks to human health, infrastructure and the surrounding environment. Thus, there may be a need in some circumstances to monitor, detect and/or measure LFG in and/or around landfills.

It is desired to address or ameliorate one or more disadvantages or limitations associated with the prior art, or to at least provide a useful alternative.

SUMMARY

Described herein is an apparatus including:
a differential pressure sensor configured to measure a pressure difference or a pressure difference change between an atmospheric air pressure and a landfill gas pressure;
a controller (a control system) configured to determine, based on the measured pressure difference or the measured pressure difference change, whether a trigger condition is met, the controller (the control system) configured to open a first valve (a bottom valve) when the trigger condition is met, thus allowing landfill gas (LFG) to enter the apparatus; and
at least one gas sensor configured to measure at least one (corresponding) gas species concentration in the LFG in the apparatus, the controller (the control system) configured to open a second valve (a top valve), before or after the at least one gas species concentration has been measured by the at least one gas sensor, (thus) allowing the LFG to flow through the apparatus.
Described herein is a method including:
measuring a pressure difference or a pressure difference change between an atmospheric air pressure and a landfill gas pressure (by a differential pressure sensor);
determining, based on the measured pressure difference or the measured pressure difference change, whether a trigger condition is met (by a controller);
opening a first valve (a bottom valve when the trigger condition is met, thus allowing landfill gas (LFG) to enter an apparatus (by the controller);

measuring at least one (corresponding) gas species concentration in the LFG in the apparatus (by at least one gas sensor); and
opening a second valve (a top valve), before or after the at least one gas species concentration has been measured by the at least one gas sensor (by the controller), thus allowing the LFG to flow through the apparatus.
The method may include (by an absolute pressure sensor of the apparatus) measuring an absolute atmospheric pressure. The method may include (by a gas flow sensor of the apparatus) measuring a LFG flow rate of the LFG flowing through the apparatus when the top valve is open.
The method may include (by the controller) closing the second valve (the top valve) to measure the at least one gas species concentration in the LFG in the apparatus (and optionally the first valve (the bottom valve)).
The apparatus may include a housing with a top end and a bottom end. The housing may house the controller, the differential pressure sensor, the absolute pressure sensor, the at least one gas sensor, the second valve (the top valve) and the first valve (the bottom valve). The housing is configured to fit into a hollow member (e.g., a pipe or tube) that extends into a landfill.
The second valve (the top valve) and the first valve (the bottom valve) may each include a solenoid valve controlled by the controller.
The at least one gas sensor may include a methane sensor and a carbon dioxide sensor.
The trigger condition may include a detection (by the differential pressure sensor) of a positive pressure difference of at least 0.1 mBar between the atmospheric air pressure and the landfill gas air pressure.
Described herein is a system including the apparatus in communication with a remote computing system via a wireless communications network.
Described herein is an apparatus (for landfill gas sensing) including:
a housing 80 configured for installation in a landfill;
a differential pressure sensor 10 and at least one gas sensor 50 in the housing 80; and
a first valve (bottom valve 40) configured to control landfill gas (LFG) gas flow to the at least one gas sensor 50,
wherein the first valve is configured to open when the differential pressure sensor 10 detects a selected pressure difference or pressure difference change between the atmospheric air pressure and the LFG pressure.
The apparatus may include an input manifold 302 in the housing 80 configured to allow landfill gas (LFG) from the landfill to flow to the differential pressure sensor 10 while the first valve (bottom valve 40) is closed.
Described herein is a method including receiving landfill gas (LFG) data generated by the method above, via a wireless communications network, representing the at least one gas species concentration in the LFG in the apparatus.

BRIEF DESCRIPTION OF THE DRAWINGS

Some embodiments of the present invention are hereinafter described, by way of non-limiting example only, with reference to the accompanying drawings, in which.

FIG. 3 is a top view of the apparatus with a top cap on;

FIG. 4 is a top view of the apparatus with the top cap removed;

FIG. 5 is an enlarged upper perspective view of a top portion of the apparatus;

FIG. 6 is a lower perspective view of the apparatus;

FIG. 7 is a side view of the apparatus;

FIGS. 11 to 21 are circuit diagrams of electronic circuits of PCBs of the internal components of the apparatus;

FIG. 27A is a rendered image of a sensor adapter of the apparatus;

FIG. 27B is a rendered image of a sensor chamber of the apparatus;

FIG. 27C is a rendered image of a valve mount of the apparatus;

DETAILED DESCRIPTION

Overview

Described herein is a system, an apparatus and a method for landfill gas (LFG) sensing (where sensing includes monitoring, detecting and/or measuring).

Figure 1A:
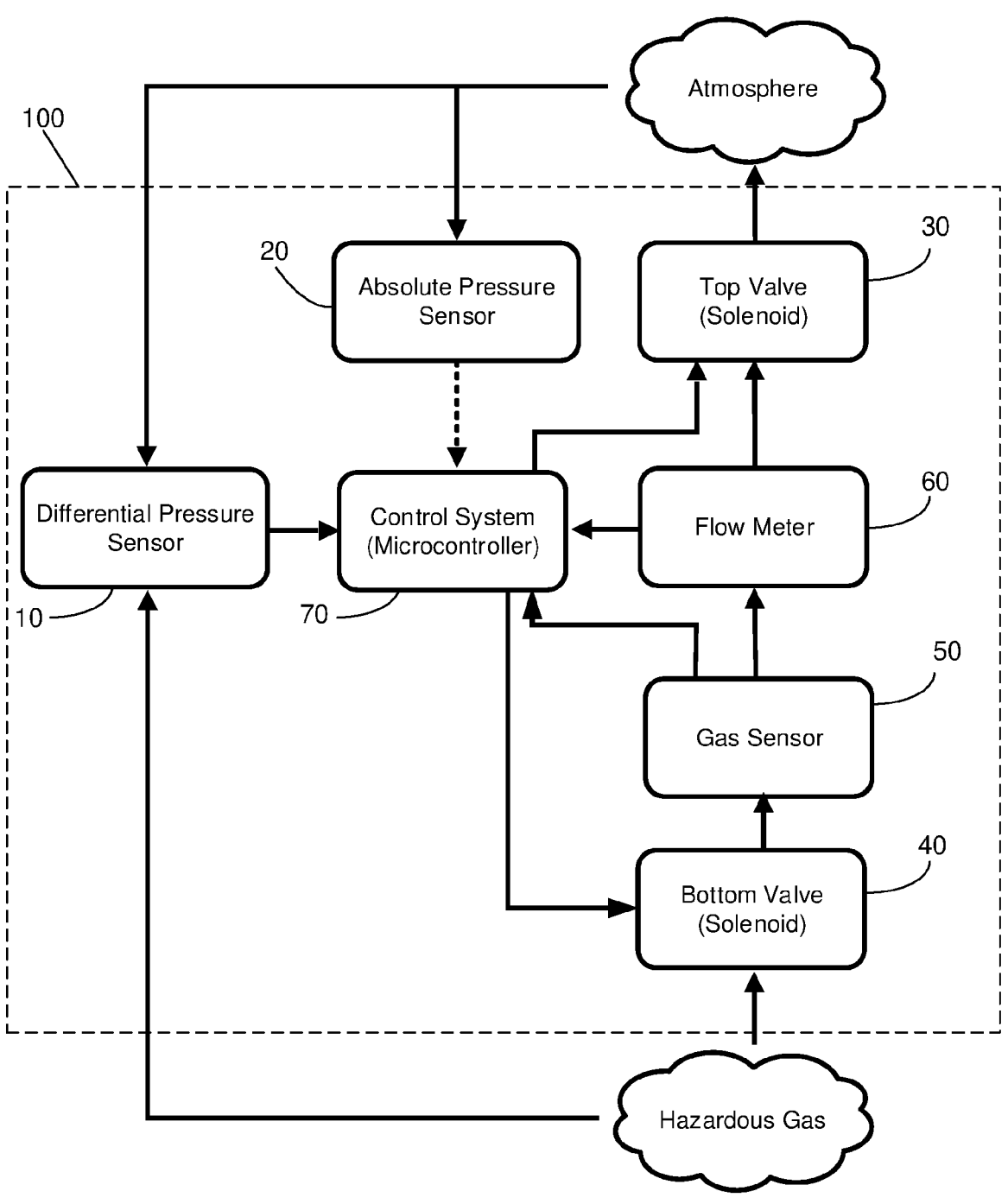
FIG. 1A is a schematic diagram of an apparatus for landfill gas (LFG) sensing.

As shown in FIG. 1A, an embodiment of the apparatus 100 includes:

a) a differential pressure sensor 10 connected to the atmospheric air;

b) an absolute pressure sensor 20 connected to the atmospheric air;

c) a first valve in the form of a bottom valve 40, where "bottom" refers to the bottom valve 40 being fluidly connected to the LFG (or "hazardous gas") substantially within a landfill via a gas inlet 91;

d) a second valve in the form of a top valve 30, where "top" refers to the top valve 30 being fluidly connected to the atmosphere, i.e., atmospheric or "fresh" or "outside" air that is substantially above the landfill;

e) at least one gas sensor 50 configured to measure concentration of at least one corresponding gas species;

f) a gas flow sensor 60 configured to measure a gas flow rate; and g) a controller in the form of a control system 70.

Figures 2A, 2B:
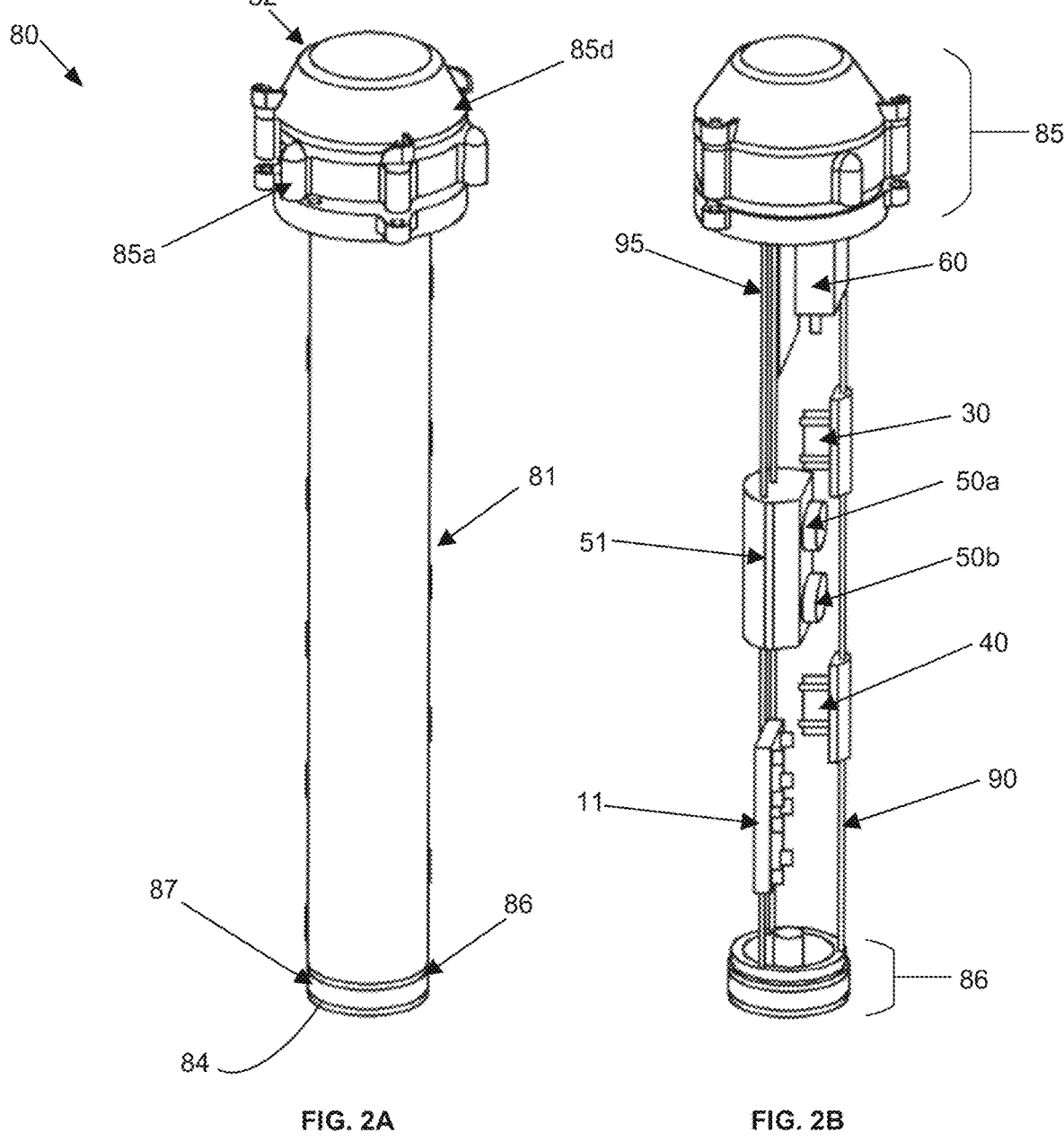
FIG. 2A is a side perspective view of the apparatus.
FIG. 2B is a side perspective view of internal components of arranged in the apparatus.

As shown in FIG. 2A, the apparatus 100 may further include a housing 80 with a top end 82 and a bottom end 84.

Figure 1B:
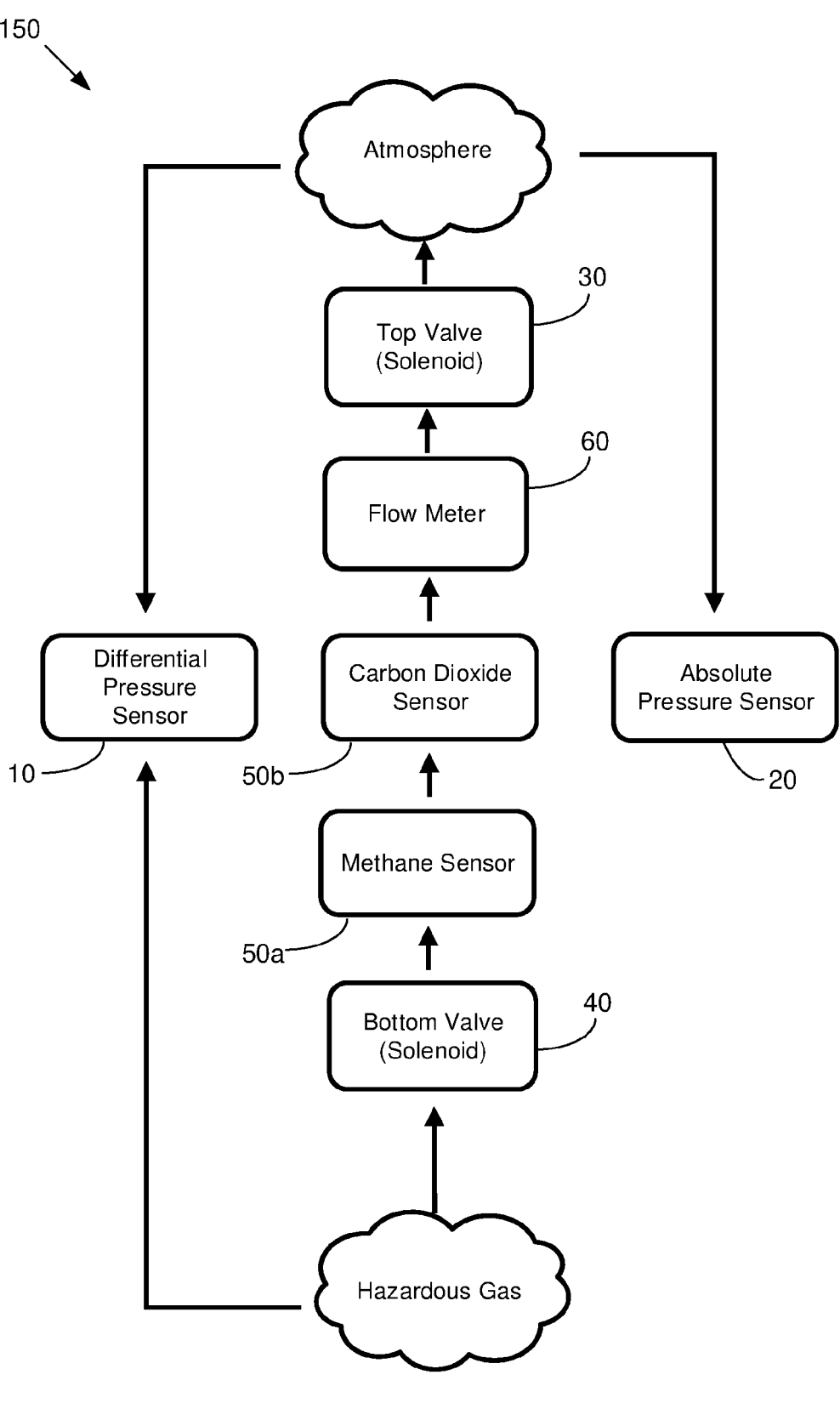
FIG. 1B is a schematic diagram of a tube network of the apparatus.
Figures 3, 4, 6, 7:
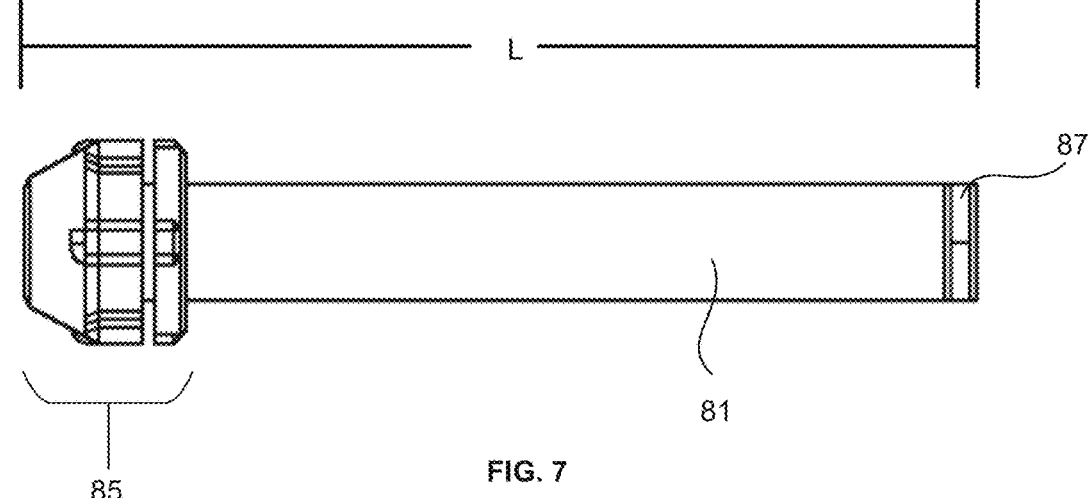
Figure 8:
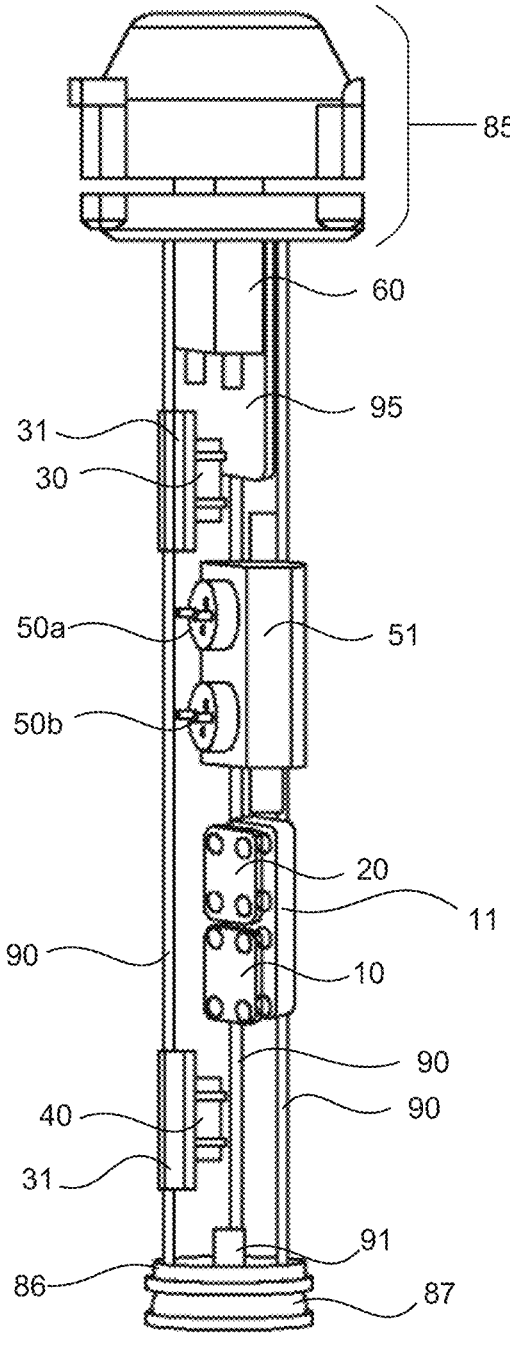
FIG. 8 is a side view of the internal components of arranged in the apparatus.
Figure 25:
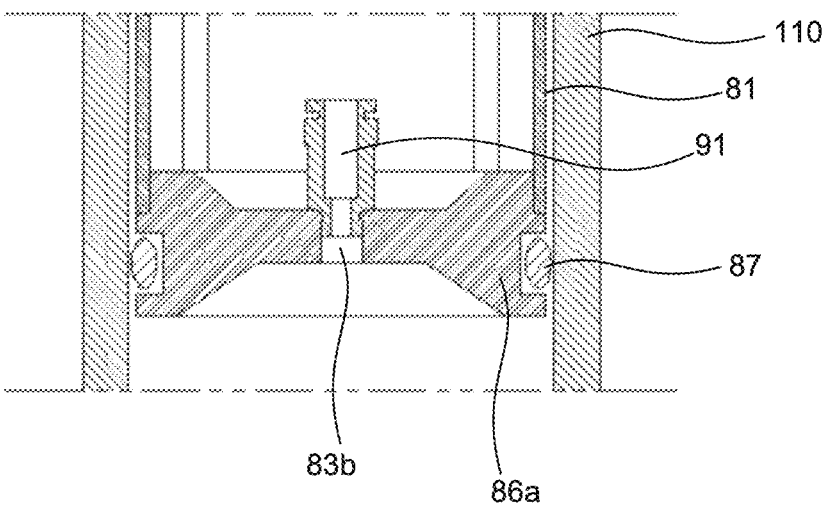
FIG. 25 is a cross-sectional view of a bottom portion of the apparatus.
Figure 30:
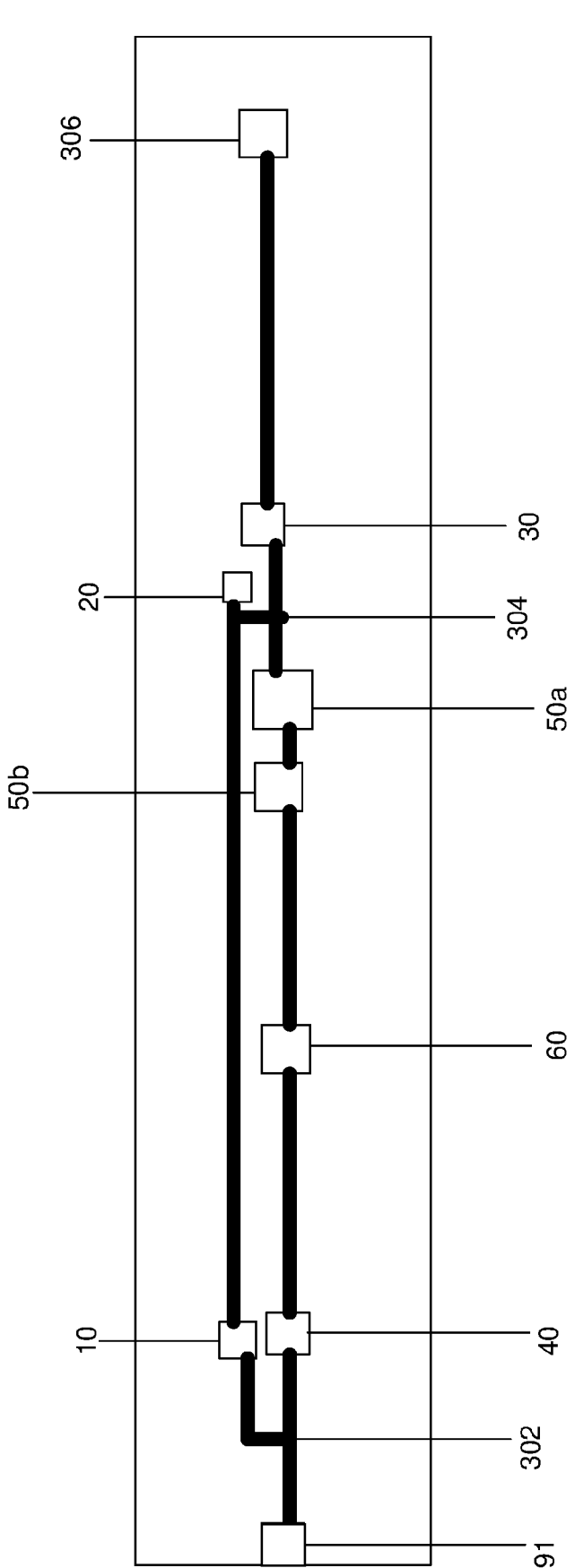
FIG. 30 is a sketch of a channel/tube network of an embodiment of the apparatus.

The apparatus 100 includes a channel/tube network 150 (also referred to herein as a "tube network", not shown in FIG. 1A) including a plurality of tubes/pipes/channels configured to control gas flow by fluidly connecting gas between the internal sensing components of the apparatus 100, as shown in FIG. 1B. The tube network 150 is configured to fluidly connect the LFG (or "hazardous gas") from within the landfill to the bottom valve 40 (via the gas inlet 91 including a gas inlet fitting, as shown in FIGS. 6, 8 and 25), and to fluidly connect the bottom valve 40 to the at least one gas sensor 50 (including a methane sensor 50a and/or a carbon dioxide sensor 50b). The tube network 150 is configured to fluidly connect the gas sensor(s) 50 to the gas flow sensor 60, and the gas flow sensor 60 to the top valve 30. The tube network 150 is configured to fluidly connect the top valve 30 to the atmospheric air. The tube network 150 fluidly connects both the atmospheric air and the LFG to the differential pressure sensor 10. The tube network 150 fluidly connects the atmospheric air to the absolute pressure sensor 20. The tubes/pipes of the tube network 150 may include channels formed in molded/printed components of the apparatus 100 (e.g., described hereinafter) and/or flexible plastic tubes with an interior diameter between 1 and 5 mm that are hermetically received by the internal components of the apparatus 100, including: the differential pressure sensor 10, the absolute pressure sensor 20, the bottom valve 40, the top valve 30, the at least one gas sensor 50 and the gas flow sensor 60. The flexible plastic tubes may include 4-mm silicone tubing and/or ⅛" silicon tubing. As shown in FIG. 30, the channel/tube network 150 may include an input manifold 302 to divide the LFG from within the landfill between the differential pressure sensor 10 and the bottom valve 40 in parallel, such that the LFG is detected by the differential pressure sensor 10 while the bottom valve 40 is closed. In some embodiments, the channel/tube network 150 may include a plurality of tubes/pipes/channels open to the atmospheric air, e.g., a tube/pipe/channel from the differential pressure sensor 10 and a separate tube/pipe/channel from the top valve 30, thus allowing the differential pressure sensor 10 to detect the atmospheric pressure while the top valve 30 is closed. In an example, the plurality of the open tubes/pipes/channels may fit in a corresponding plurality of tube channels 180b, 180c described with reference to FIG. 28E below. In other embodiments, the channel/tube network 150 may include only one tube/pipe/channel that is open to the atmospheric air, forming a unitary gas outlet 306 (as shown in FIG. 30), and an output manifold 304 may be arranged to connect the tubes/pipes/channels from the unitary gas outlet 306 to both the differential pressure sensor 10 and the sensors (including the at least one gas sensor 50 and the gas flow sensor 60) in parallel. For example, as shown in FIG. 30, the channel/tube network 150 may include the unitary gas outlet 306, the output manifold 304 to divide the atmospheric air between the differential pressure sensor 10 and the sensors (including the at least one gas sensor 50 and the gas flow sensor 60) in parallel. The unitary gas outlet 306 may be of use when connecting the apparatus 100 to other gas monitoring equipment so that all of the gas flow through the tube network 150 flows from one outlet when in use. In embodiments with the output manifold 304, the top valve 30 may be connected between the unitary gas outlet 306 and both of the differential pressure sensor 10 and the sensors (and optionally the absolute pressure sensor 20), as shown in FIG. 30, such that the atmospheric pressure is only detected by the differential pressure sensor 10 (and optionally the absolute pressure sensor 20) when the top valve 30 is open—and in these embodiments, the top value 30 is controlled by the control system 70 to be open while the differential pressure sensor 10 is monitoring/detecting the differential pressure, which can be most of the time.

The method includes:

a) in embodiments where the top valve 30 is connected between the unitary gas outlet 306 and the differential pressure sensor 10, e.g., as shown in FIG. 30, the top valve 30 being opened or being left open;

b) the absolute pressure sensor 20 sensing the atmospheric or "fresh" or "outside" air pressure that is substantially above the landfill;

c) the differential pressure sensor 10 measuring a pressure difference between the atmospheric air pressure and the landfill gas pressure of the LFG substantially within the landfill, and determining whether a trigger condition is met;

d) the control system 70 opening the bottom valve 40 when the trigger condition is met, thus allowing LFG to enter the apparatus 100;

e) the control system 70 closing the top value 30 (if it is open) and the at least one gas sensor 50 measuring at least one corresponding gas species concentration in the LFG in the apparatus 100 (and the control system 70 respectively reading the at least one gas species concentration from the at least one gas sensor 50);

f) the control system 70 opening the top valve 30 when the at least one gas species concentration has been measured by the at least one gas concentration sensor 50, thus allowing the LFG to flow through the apparatus 100; and g) once the top valve 30 has been opened, or before it is closed, the gas flow sensor 60 measuring a LFG flow rate of the LFG through the apparatus 100 (which may be before or after the measuring of the at least one corresponding gas species concentration).

In embodiments, the control system 70 may open the top value 30 (or leave it open) when the control system 70 opens the bottom value 40, and may then measure the LFG flow rate (with the gas flow sensor 60) before closing the top value 30 and measuring the at least one gas species concentration. In these embodiments, it may save power to have the top valve 30 open most of the time, closing it only to make the gas species concentration measurements. In these embodiments, the bottom value 40 is closed most of the time, being opened only to make the gas species concentration measurements. The apparatus 100 makes use of natural environmental pressure differences between the surface of the landfill and within the landfill, specifically at the depth to which the hollow member penetrates. Accordingly, the apparatus 100 need not require battery power to draw the LFG to the at least one gas sensor, e.g., in contrast to traditional LFG monitoring apparatuses. The method for LFG sensing may therefore be referred to as a "fanless" or "pumpless" extraction method because the apparatus 100 operates without a fan or pump to draw/push the LFG to the at least one gas sensor.

The top valve 30 can mitigate air flowing down through the apparatus 100, i.e., in the "wrong" direction, which might otherwise occur if the atmospheric air pressure is higher than the landfill air pressure, which may occur due to certain atmospheric conditions, e.g., a high pressure air mass.

Trigger Condition

Figure 22:
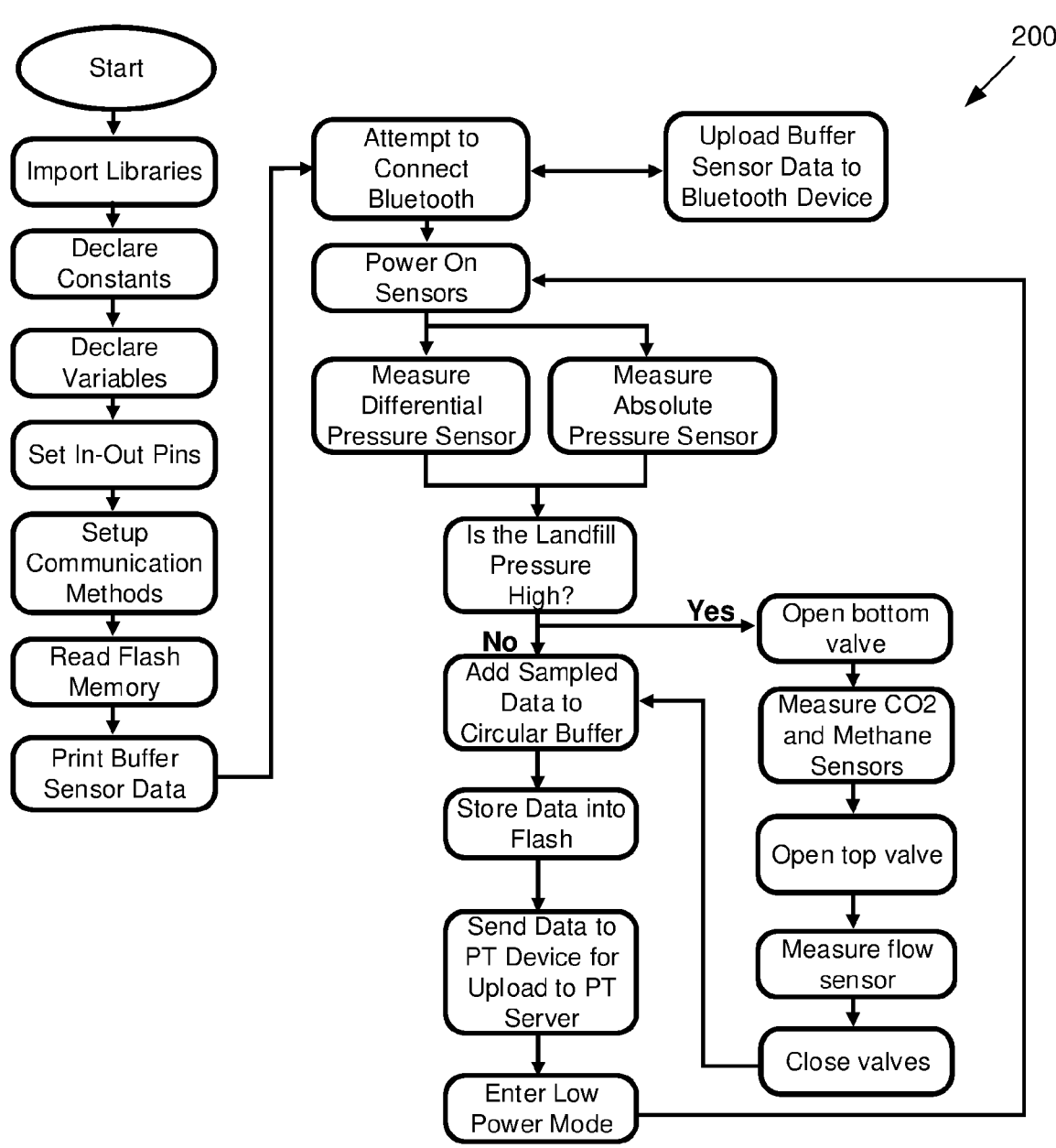
FIG. 22 is a flow diagram of a method for LFG sensing.

The trigger condition can be met when a selected pressure difference or pressure difference change between the atmospheric air pressure and the LFG pressure is detected by the differential pressure sensor 10. The trigger condition can be met when the pressure difference between the atmospheric air pressure and the landfill air pressure, detected by the differential pressure sensor 10, is substantially above a minimum pressure difference of 0.001 millibar (mBar), so the settable differential pressure trigger point (i.e., the selected pressure value) can be 0.001 mBar or above. Alternatively, the trigger condition may be based on the pressure difference change in the differential pressure detected by the differential pressure sensor. The trigger condition can be selected such that the following elements are only activated when there is a substantial pressure differential, or a substantial change in the differential pressure, between the ends of the apparatus 100 (e.g., more than 1%, 2%, 5% or 10%), thus using power and generating measurements only when conditions of interest are met, thus mitigating electrical power usage in the apparatus 100 by electronic components including: the top valve 30, the bottom valve 40; the at least one gas sensor 50; the gas flow sensor 60; and the control system 70. Accordingly, in some implementations, the apparatus 100 and the method only generate measurement data when conditions are relevant for the purposes of monitoring risk and/or gas availability (e.g., relevant for toxicity and/or energy extraction), e.g., where the gas is methane. As shown in FIG. 22, and further described below, in some embodiments the trigger condition can be used to switch the control system 70 from a low power mode to a sensing mode.

Housing

Figure 24:
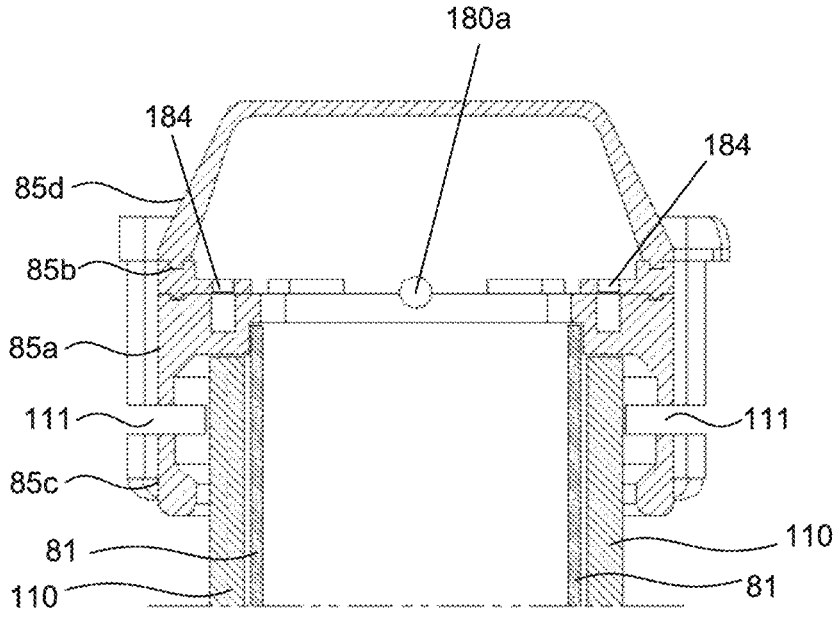
FIG. 24 is a cross-sectional view of the top portion of the apparatus.

As shown in FIGS. 24 and 25, the housing 80 includes a tube 81 which is configured to fit into a hollow member 110 (e.g., a pipe or tube or 'monitoring well') that extends into and is installed in the landfill, e.g., into a LFG borehole, 'stand pipe' or 'Gattic well'.

The hollow member 110 can be a pipe with an internal cross section that is substantially 50 mm or 100 mm across, e.g., a circular pipe with a 50-mm or 100-mm internal diameter. The hollow member 110 can be over 1 m long, e.g., over 10 m, over 15 m or over 20 m long. The hollow member 110 can extend to a depth over 1 m into the landfill from a surface of the landfill, e.g., over 10 m, over 15 m or over 20 m in. The hollow member 110 is sufficiently long to substantially mitigate gas short circuiting, i.e., when atmospheric air from outside the landfill penetrates the landfill to a depth greater than the depth of the hollow member 110.

For example, the hollow member 110 may be a pipe or tube with a nominal size of DN50 and a pressure rating of PN18, e.g., 2 inches in diameter, e.g., a standard DN50PN18 pressure pipe, a common land fill gas borehole size.

As shown in FIGS. 2A, 6, 7, 24 and 25, the housing 80 includes the tube 81 that may be inserted into and removed from the hollow member 110. That is, a greatest external diameter of the tube 81 may smaller than a smallest internal diameter of the hollow member 110, so that at least a portion of the tube 81 can fit inside the hollow member 110, as shown in FIGS. 24 and 25. The tube 81 may be a stainless steel tube (e.g., 314 stainless steel) with a thickness of approximately 1.6 mm and an external diameter of 48 mm (e.g., to allow it to fit inside a hollow member 110 with a diameter of 50 mm). Alternatively, the tube 81 may be a carbon fibre tube. The housing, including the tube 81 and the top piece 85, may have a length L, e.g., as shown in FIG. 7, of between 100 mm and 1 m, including at least 200 mm, 300 mm, or 400 mm, and/or less than 800 mm, 700 mm, 600 mm, or 400 mm, e.g., substantially 390 mm, 560 mm or 690 mm.

As shown in FIGS. 2B and 6, the housing 80 may include a top portion 85 located at the top end 82 of the housing. As shown in FIGS. 28A to 28D, the top portion 85 can include: a middle piece 85a, a spacer 85b, a clamp 85c and a removably attached top cap 85d.

Figures 28A, 28B, 28C, 28D:
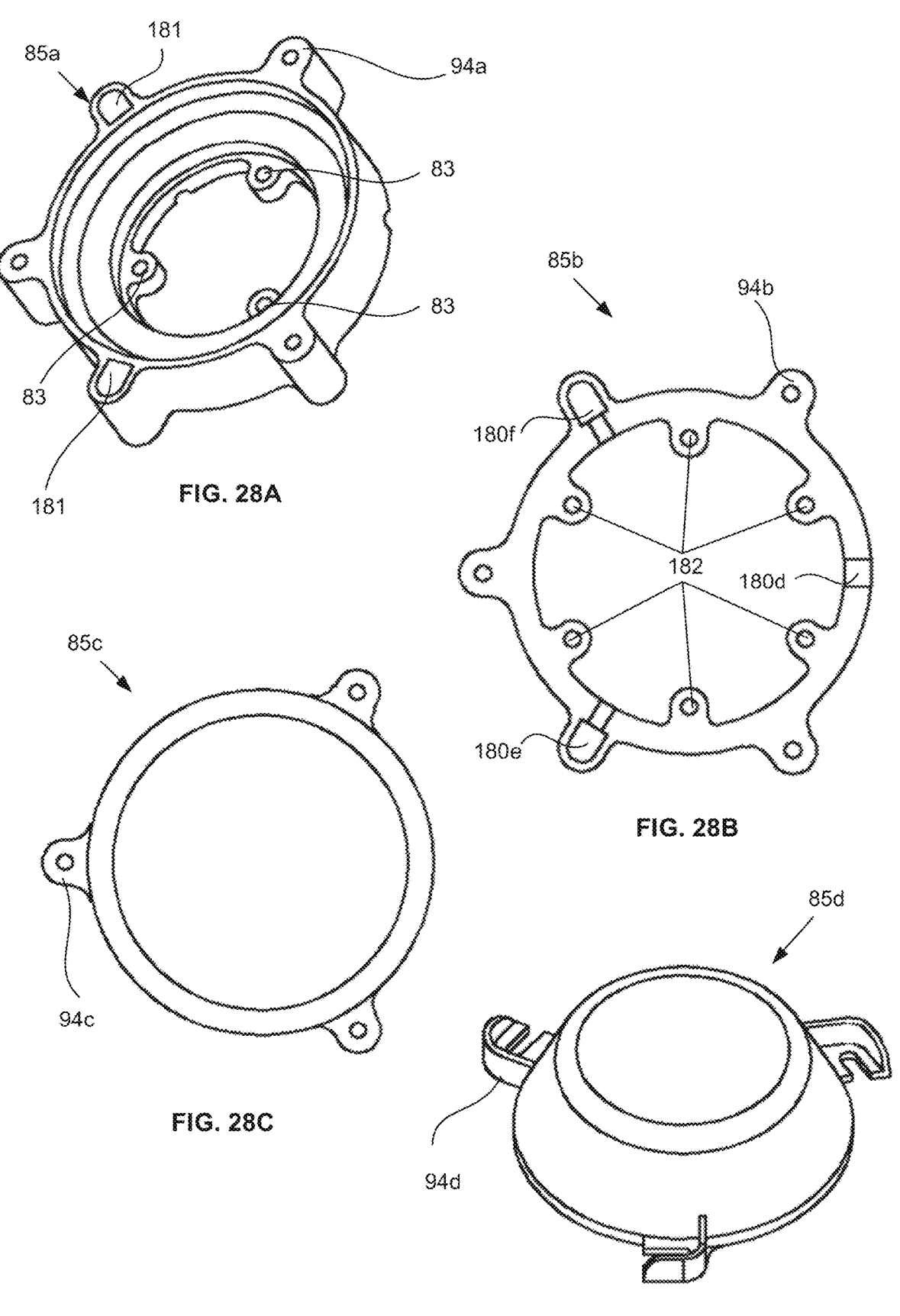
FIGS. 28A to 28D respectively are rendered images of a middle piece, a spacer, a clamp and a top cap of the top portion of the apparatus.
Figure 28E:
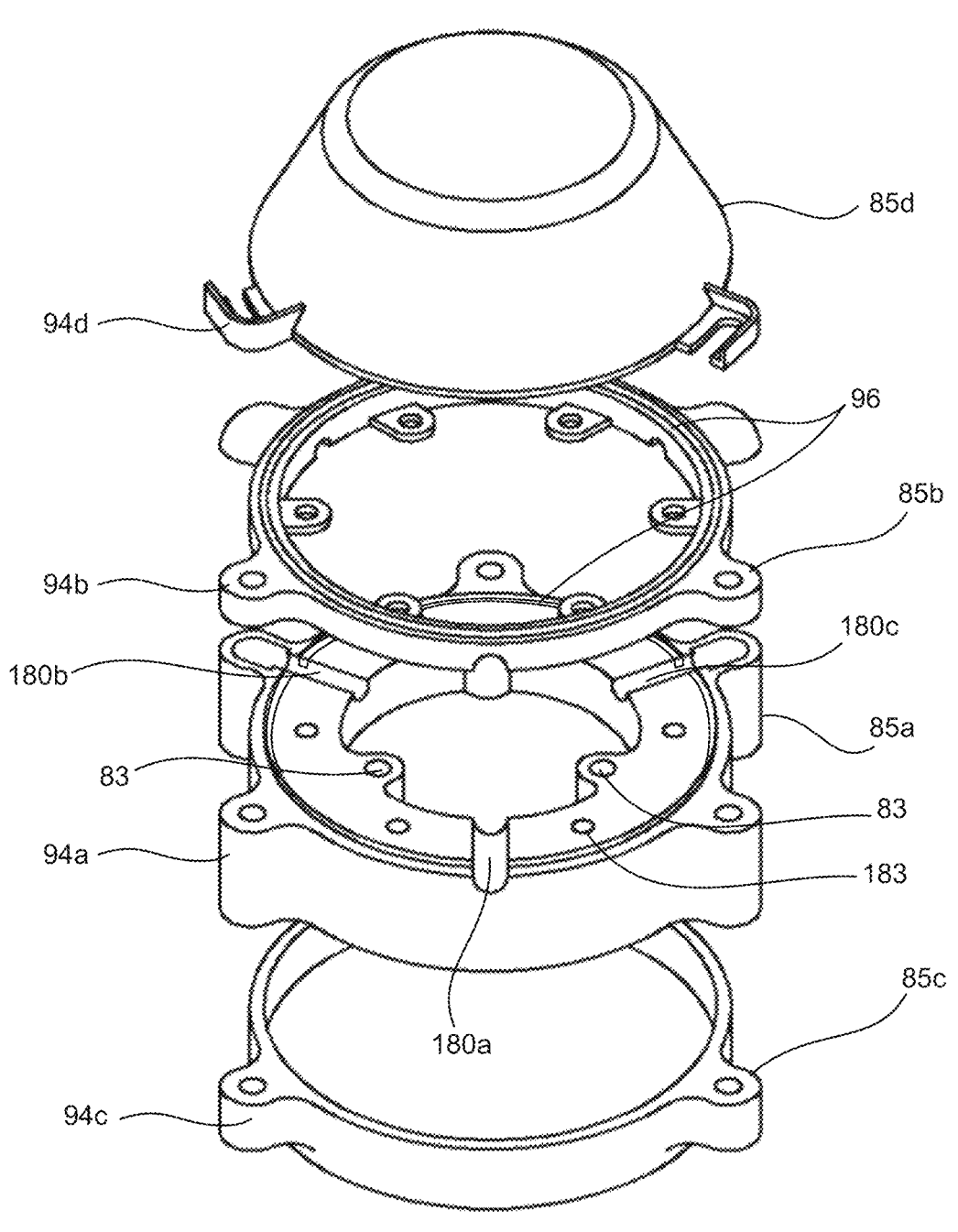
FIG. 28E is an exploded upper side view of the middle piece, the spacer, the clamp and the top cap.

As shown in FIG. 28E, the middle piece 85a includes a cable channel 180a and two tube channels 180b, 180c. The cable channel 180a is configured to carry a cable 92a from inside the housing 80 to outside the housing 80 to connect the internal sensing components to a communication device 92 of the apparatus 100 (shown in FIG. 10 and further described hereinafter) that is external to the housing 80 so the communication device 92 can communicate with a remote computing system without needing to transmit signals through the housing 80 or the hollow member 110 as described further hereinafter. The plurality of tube channels 180b, 180c are configured to receive upper ends of the tubes of the tube network 150, where the upper ends are open to the atmospheric air, i.e., the tubes that connect fluidly to the differential pressure sensor 10, the absolute pressure sensor 20 and the top valve 30 as shown in FIG. 1B. As shown in FIG. 28E, the spacer 85b fits directly onto the middle piece 85a. When in place, the spacer 85b holds the cable 92a and the upper ends of the two tubes into the respective cable channel 180a and tube channels 180b, 180c, optionally with respective channels 180d, 180e, 180f formed in the spacer 85b as shown in FIG. 28B that cooperate to hold the cable 92a and two tubes. The cable channel 180a opens sideways from the housing 80 when in use, i.e., horizontally, as shown in FIG. 24. The tube channels 180b, 180c connect to downward channels 181, formed in the middle piece 85a as shown in FIG. 28A, that face downward from the housing 80 when in use, e.g., to mitigate rain entering the tube channels 180b, 180c and thus the tube network 150. As shown in FIG. 28B, the spacer 85b includes a plurality (6) of flanges 182 extending horizontally and radially inward from a circular body of the spacer 85b. As shown in FIG. 28E, these flanges 182 align with a face 183 of the middle piece 85a when in place. As shown in FIG. 24, fasteners 184 (e.g., bolts) can hold the spacer 85b to the middle piece 85a when in use by extending through the flanges 182 into the face 183 of the middle piece 85a, thus holding the cable 92a in the cable channel 180a and the tubes in the tube channels 180b, 180c when assembled.

As shown in FIGS. 3 to 8, the top cap 85d may attach to the remainder of the top portion 85 by one or more fasteners 93 (such as screws) which can be loosened or unfastened so that the top cap 85d can be removed (by counter-clockwise rotation) to access inside the housing 80 and tightened or re-fastened once the top cap 85d has been replaced (by clockwise rotation). Alternatively, the top cap 85d may attach to the remainder of the top portion 85 by a thread around a circumference of the opening of the top cap 85d that engages cooperatively with a corresponding thread around a circumference of the remainder of the top portion 85 such that the top cap 85d can be manually loosened or unfastened by twisting the top cap 85d (in a first direction, e.g., counter-clockwise rotation) to access inside the housing 80 and tightened or re-fastened by twisting the top cap 85d (in a second direction opposite to the first direction, e.g., clockwise rotation). The top cap 85d may include or be formed of a transparent material, allowing components inside the top portion 85 to be visible without removal of the top cap 85d. As shown in FIG. 28E, the middle piece 85a, spacer 85b, clamp 85c and top cap 85d each have three corresponding outer flanges 94a, 94b, 94c and 94d that mutually align when the top portion 85 is assembled. The flanges 94a-c have cooperating apertures that allow the fasteners 93 to secure the middle piece 85a, spacer 85b and clamp 85c together, while the flanges 94d on the top cap 84d have cooperating slots (each with an open end) to allow the top cap 95d to be removed by rotation when the fasteners 93 are loosened or unfastened without requiring complete removal of the fasteners 93 (in contrast to the middle piece 85a, the spacer 85b and the clamp 85c which are held in place when the fasteners 93 are loosened, and require removal of the fasteners 93 for mutual disassembly).

Figures 29A, 29B:
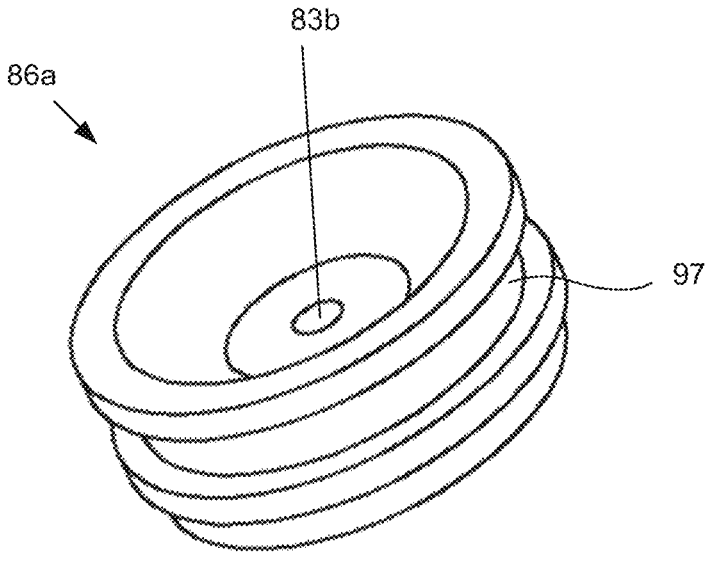
FIGS. 29A and 29B respectively are rendered images of a bottom perspective view and a top perspective view of a bottom piece of the apparatus.

As shown in FIG. 2B, the housing 80 may include one or more rods 90 extending between the top portion 85 of the housing 80 and the bottom portion 86 of the housing 80. Each rod 90 may be fastened to the top portion 85 of the housing 80 by a fastener (not shown). The one or more rods 90 may strengthen the mechanical support and integrity of the housing 80, so that the housing 80 can be pushed into and pulled out of the hollow member by a user. The rods 90 pass through apertures 83 of the top portion 85 (e.g., apertures 83 in the middle piece 85a). The rods 90 may be threaded rods that are fastened to the top portion 85 by threaded fasteners of a corresponding size. For example, each rod 90 may be a M3 threaded rod (i.e., a threaded rod with a nominal outer diameter of 3 mm) and each corresponding fastener may be a M3 nut. The rods 90 are also secured to respective sockets 83a in the bottom portion 86, as shown in FIG. 29B, by respective fasteners, e.g., M3 nuts. The rods 90 support the other components of the apparatus 100, including the sensing components, with each component being mounted on an adapter with one or more apertures through which pass one or more of the rods 90, and each adapter is fixed to the rods 90, e.g., by fasteners, e.g., M2 or M3 nuts and bolts.

The housing 80 includes the bottom portion 86 at the bottom end. As shown in FIGS. 25, 29A and 29B, the bottom portion 86 includes a bottom piece 86a (also referred to as a 'bottom plug') with a central through hole 83b of the gas inlet 91 (i.e., a fluid conductor though the bottom portion 86, located substantially centrally in a bottom face of the bottom piece 86a) in which the gas inlet fitting of the gas inlet 91 is provided. The gas inlet 91 is configured to allow LFG to enter the housing 80 at the bottom end 84 into the tube network 150. The bottom piece 86a may be 3D printed using nylon.

As shown in FIG. 25, the bottom portion 86 includes an external seal 87 (also referred to as the 'first seal' or 'inner seal') configured to seal the housing 80 in the hollow member 110 be pressing against a (substantially circular) inner surface of the hollow member 110 as shown in FIG. 25. The external seal 87 prevents air, and in particular LFG, flowing around the apparatus 100 rather than through the apparatus 100. The external seal 87 may be an O-ring. The O-ring may sit within a groove 97 of the bottom portion 86. The O-ring may be made out of a rubber material such as FKM. FKM may be more chemically resistant than rubbers such as nitrile and neoprene.

The top portion 85 of the housing 80 may include a second seal 111 (or 'upper seal' or 'outer seal') at or towards the top end 82 of the housing 80, clamped between the middle piece 85a and the clamp 85c, and seated or fitted around a (substantially circular) outer surface of the hollow member 110, as shown in FIG. 24. The second seal 111 may be an O-ring seal. The second seal 111 seals the housing 80 to the hollow member 110 by pressing against the outer surface of the hollow member 110 by natural resilience of the second seal 111, and by being pressed between continuous (circular) portions of the middle piece 85a and the clamp 85c when the middle piece 85a and the clamp 85c are forced together by the fasteners 93 (i.e., when the fasteners 93 are fastened as in normal use). The second seal 111 may be a nitrile seal. The second seal 111 may function as a 'back-up seal'. For example, if the external seal 87 fails, the second seal 111 can act as a back-up seal between the atmosphere and the LFG bore. The second seal 111 may include polyvinyl chloride (PVC).

When the housing 80 is inserted into the hollow member, it may be removably fastened to the hollow member 110 by one or more fasteners. For example, the housing 80 may be removably fastened to the hollow member by fasteners that are bolts located on the top portion 85 of the housing 80, e.g. the fasteners 93. The fasteners can then be unfastened in order to remove the apparatus 100 from the hollow member 110. As shown in FIG. 24, the fasteners may clamp the housing 80 to the hollow member 110 by forcing the clamp 85c towards the middle piece 85a, thus clamping the second seal 111, which holds onto the hollow member 110 by its natural resilience (including when the fasteners are loosened to rotationally remove the top cap 85d).

The apparatus 100 may be substantially weather-proof so that it can operate in the humid and/or damp conditions of a landfill. The apparatus 100 may include one or more features for mitigating water ingress into the housing 80, such as one or more of: the top cap 85d, the first seal 87, the second seal 111, and power supply seals to mitigate water reaching the internal sensing components (such as O-rings which sit in respective upward facing ring grooves 96 of the spacer 85b and the middle piece 85a), and the downward facing channels 181.

Valves

The apparatus 100 includes the top valve 30 and the bottom valve 40. The valves are enclosed by and/or attached to the housing 80. As shown in FIG. 8, the top valve 30 is closer to the top end 82 of the housing 80 than the bottom valve 40, while the bottom valve 40 is closer to the bottom end 84 of the housing 80 than the top valve 30. Either or both of the valves 30,40 may be attached to one or more of the rods 90 of the housing 80 using respective adapters.

The top valve 30 and the bottom valve 40 may each include a solenoid valve that is controlled by the control system 70. For example, the top valve 30 and/or the bottom valve 40 may be Parker X-Valve Miniature Pneumatic Solenoid Valves. The solenoid valves can be controlled by metal oxide semiconductor field effect transistors (MOSFETs) such as PMF250XNEX Nexperia MOSFETs.

Figure 18:
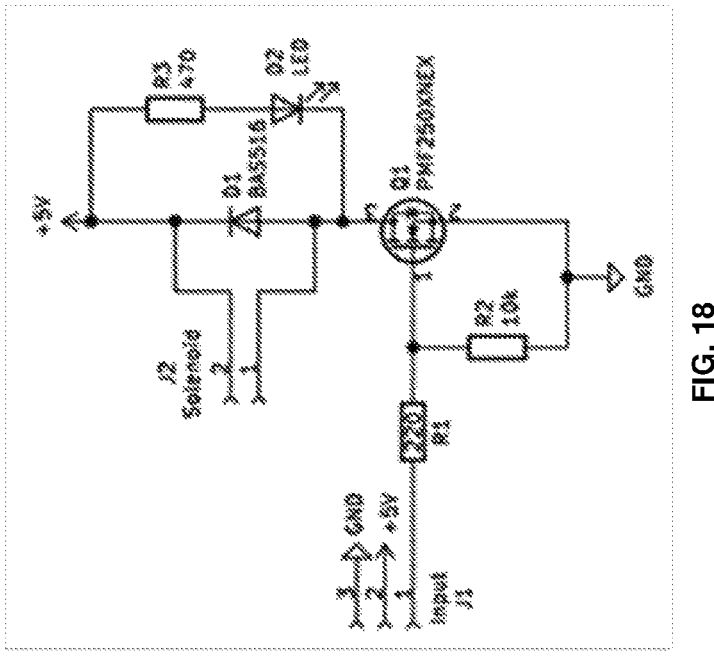

The solenoid valves may each be mounted onto valve PCBs, i.e., a top valve PCB and a bottom valve PCB. Each of the valve PCB s may include a visual indicator in the corresponding circuit, as shown in FIG. 18, such as an LED to indicate the state of the mounted solenoid valve, i.e., open or closed. The visual indicator may be mounted under the top cap 85d that includes or is formed of the transparent material. Each valve PCB may be affixed to a valve adapter 31, which is mounted to at least one of the rods 90. As shown in FIG. 27C, the valve adapter 31 may include a longitudinal channel or socket 27a configured to fit around one of the rods 90. The valve adapter 31 may be 3D printed using nylon.

Sensors

Figure 19:
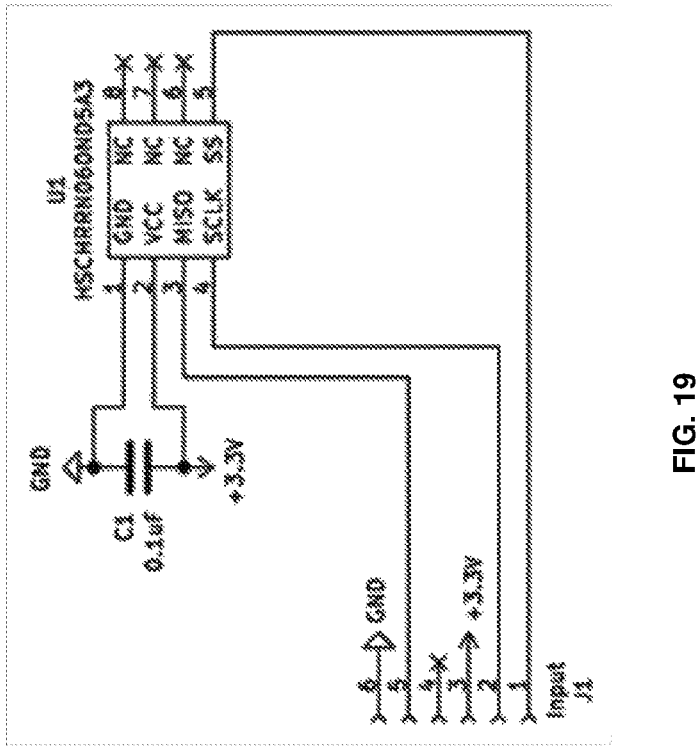

The differential pressure sensor 10 measures a pressure difference between an atmospheric pressure (above the apparatus 100 or otherwise substantially outside of the landfill) and a landfill gas pressure (below the apparatus or otherwise substantially in the landfill). The differential pressure sensor 10 returns an electronic signal in the form of a voltage value, corresponding to a change in the pressure difference, to the control system 70. The differential pressure sensor 10 may be, for example, a Honeywell HSCMRRN060MDSA3 differential pressure sensor configured to operate on a 3.3 V source voltage with passive filtering. The differential pressure sensor 10 may be mounted on a differential pressure PCB in an electronic circuit, as shown in FIG. 19. The differential pressure sensor 10 and the differential pressure PCB are mounted to at least one of the rods 90, e.g., below the bottom valve 40, via an adapter.

Figure 20:
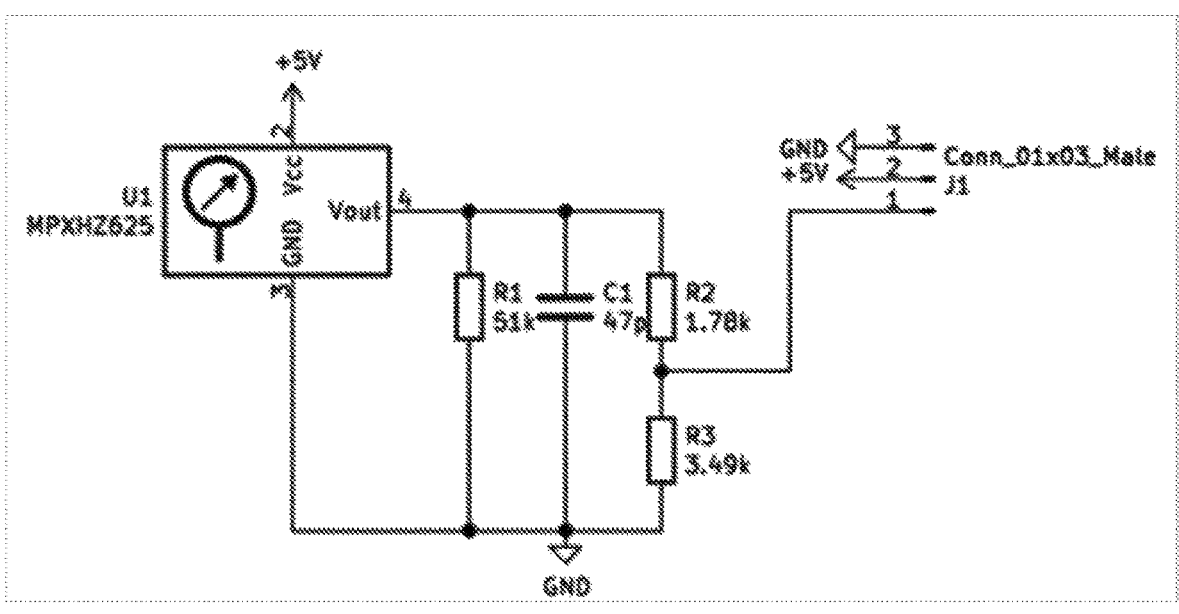

The absolute pressure sensor 20 measures an atmospheric pressure above the apparatus 100 (i.e., above ground or otherwise substantially outside the landfill). The absolute pressure sensor 20 returns an electronic signal in the form of a direct analogue voltage output, corresponding to a pressure change, to an analogue input of the control system 70. The absolute pressure sensor 20 may be, for example, a NXP USA Inc. MPXHZ6250AC6T1 absolute pressure sensor configured to operate on a 5 V source voltage with passive filtering. The absolute pressure sensor 20 may be mounted on an absolute pressure PCB in an electronic circuit, as shown in FIG. 20. The absolute pressure sensor 20 and the absolute pressure PCB is mounted to the housing 80. It may be mounted to one of the rods 90, e.g., below the bottom valve 40 and the differential pressure sensor 10.

The differential pressure sensor 10 (and differential pressure PCB) and the absolute pressure sensor 20 (and absolute pressure PCB) can be affixed to a single sensor adapter 11 for mounting to two of the rods 90 of the housing 80. As shown in FIG. 27A, the single sensor adapter 11 includes a plurality of mutually parallel longitudinal channels or sockets 27b configured to fit around a corresponding plurality of the rods 90. As shown in FIG. 27A, the single sensor adapter 11 includes a plurality of raised portions or bumps to fasten the sensors 10,20 and PCBs thereto. The sensor adapter 11 may be 3D printed using nylon.

Figure 21:
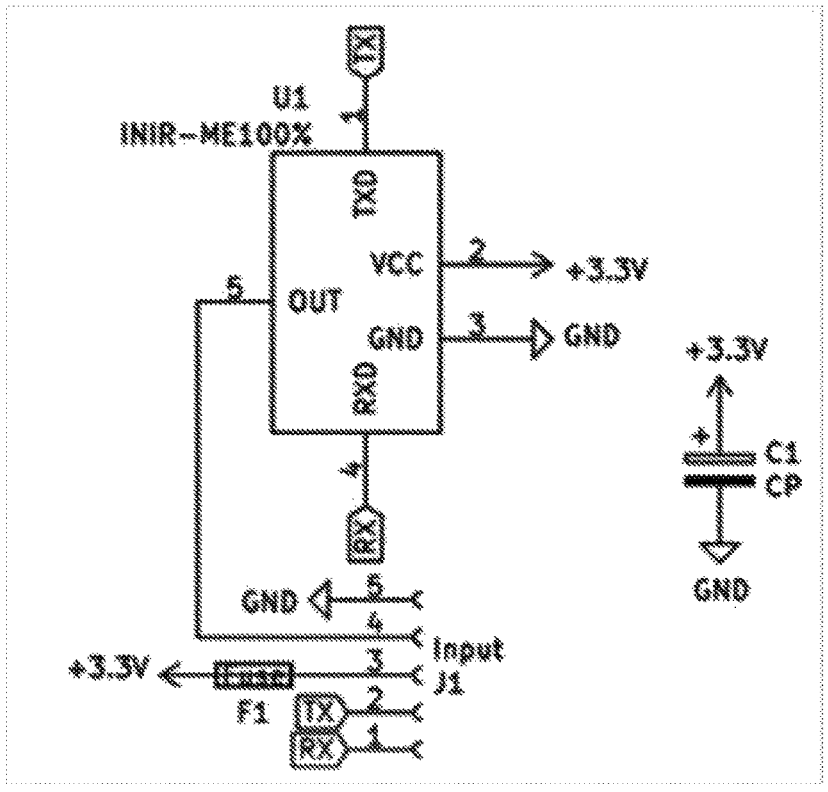

The at least one gas sensor 50 is configured to measure concentration of at least one corresponding gas species in the LFG that enters the apparatus 100 via the bottom valve 40. Where there are a plurality of the gas sensors, each respective gas sensor 50 may measure concentration of a respective corresponding gas species. Two or more of the plurality of the gas sensors may be arranged in series, thus the LFG passes through a first one of the gas sensors into a pipe/tube mutually connecting the gas sensors, and from the connecting pipe/tube into a second one of the gas sensors (and into a further connecting pipe/tube and third one if there are three gas sensors, etc.). The two or more of the gas sensors may be arranged in series along the length of the housing 80 such that a further gas sensor may added in series to the two or more gas sensors without needing to move the two or more gas sensors, or reconfigure the tube network 150, apart from inserting the further gas sensor in series. The at least one gas sensor 50 can include one or more of a methane ($CH_4$) sensor 50a and a carbon dioxide ($CO_2$) sensor 50b. For example, the at least one gas sensor 50 could be one or more of a SGX Sensortech INIR-ME100% (for measuring concentration of $CH_4$) and a SGX Sensortech INIR-CD5% (for measuring concentration of $CO_2$). The gas sensors 50 may each operate on a 3.3 V voltage source and produce an analogue voltage output, e.g., 1.25 V corresponding to 0% of the respective gas species and 2.5 V corresponding to the maximum of the sensor's range (e.g., 100% $CH_4$ for the INIR-ME100% and 5% $CO_2$ for the NIR-CD5%). The at least one gas sensor 50 may be mounted on a gas sensor PCB, as shown in FIG. 21. If there is more than one gas sensor 50 then there may be a plurality of gas sensor PCBs with one corresponding to each gas sensor. The at least one gas sensor 50 is mounted to, and housed by, a sensor chamber 51. The sensor chamber 51 allows for a secure connection between the tube network 150 and the at least one gas sensor 50, and allows the sensor(s) 50 to be appropriately exposed to the landfill gas passing through the tube network 150 for accurate measurements. The sensor chamber 51 is connected to the tube network 150 by an inlet and an outlet 28. As shown in FIG. 27B, the sensor chamber 51 includes an adapter in the form of a plurality of mutually parallel longitudinal channels or sockets 27c configured to fit around a corresponding plurality of the rods 90. As shown in FIG. 27B, the sensor chamber 51 includes a plurality of chambers 28a configured to hold the gas sensor(s) 50. The sensor chamber 51 is mounted between the top valve 30 and the bottom valve 40. The sensor chamber 51 may be 3D printed using nylon.

The gas flow sensor 60 is configured to measure a gas flow rate inside the housing 80. The gas flow sensor 60 may be, for example, a Sensirion ASF1400 mass flow sensor. The gas flow sensor 60 may operate on a 9 V voltage source and communicate with the control system using an RS-232 standard, e.g., using an RS-232-TTL converter module such as a MAX3232. A PMF250XNEX MOSFET may be used to turn the gas flow sensor 60 on and off. The gas flow sensor 60 is located inside the housing 80 above the top valve 30, so that it can detect flow of LFG moving upwards through the top valve 30, and may be mounted to a bottom side of the main PCB 95 (described hereinafter).

Control System

As shown in FIG. 1, the control system 70 includes electronic connections such that it is in electronic communication with the differential pressure sensor 10, the absolute pressure sensor 20, the top valve 30, the bottom valve 40, the at least one gas sensor 50 and the gas flow sensor 60.

The control system 70 can include a microcontroller 3 that is mounted on a main PCB 95. The microcontroller 3 has a microprocessor and memory, and may have a Bluetooth/Bluetooth Low Energy module. The microcontroller 3 can be a commercially available Adafruit Feather M0 Bluefruit.

Figures 9A, 9B:
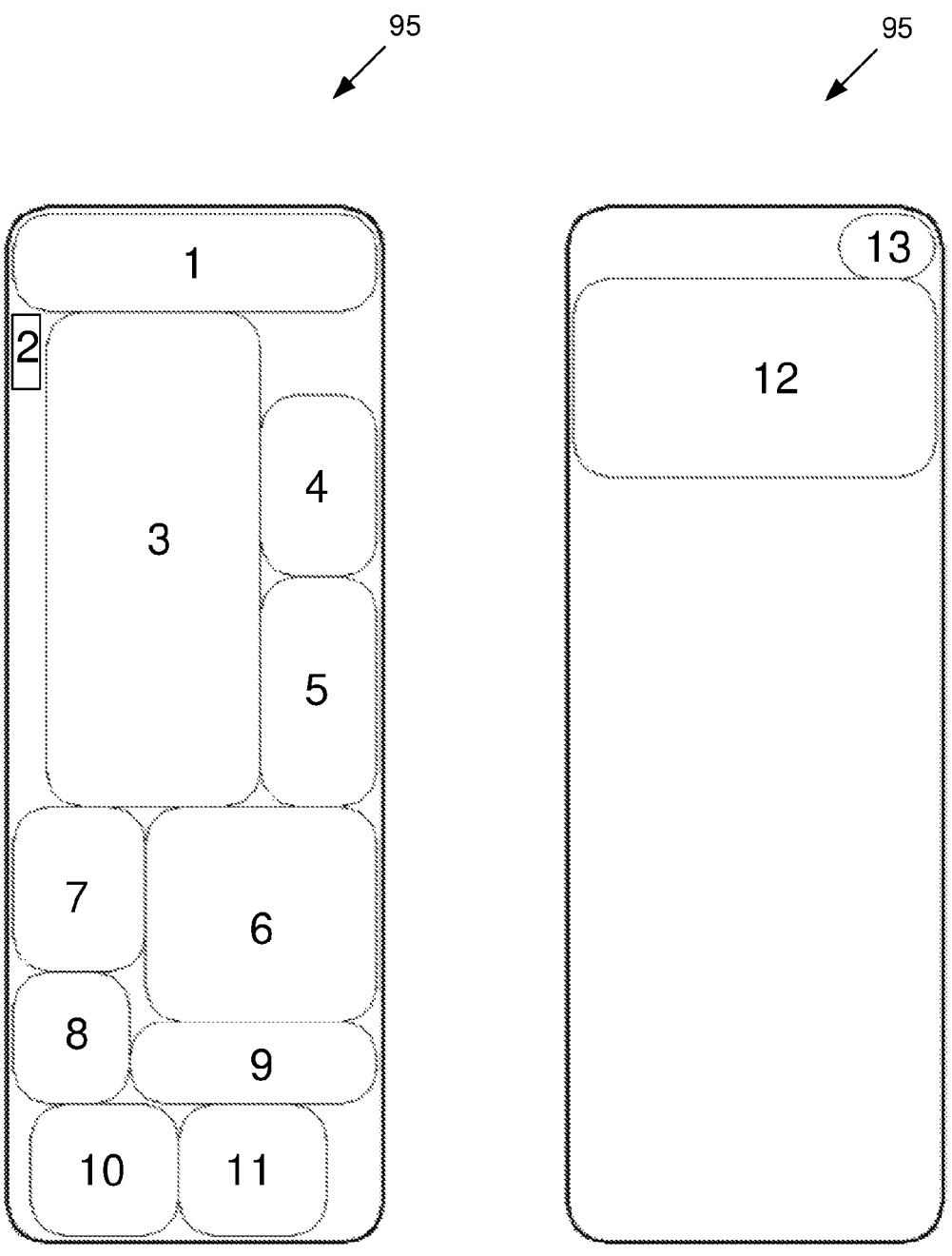
FIGS. 9A and 9B are front and rear views of a main printed circuit board (PCB) of the apparatus.
Figure 11:
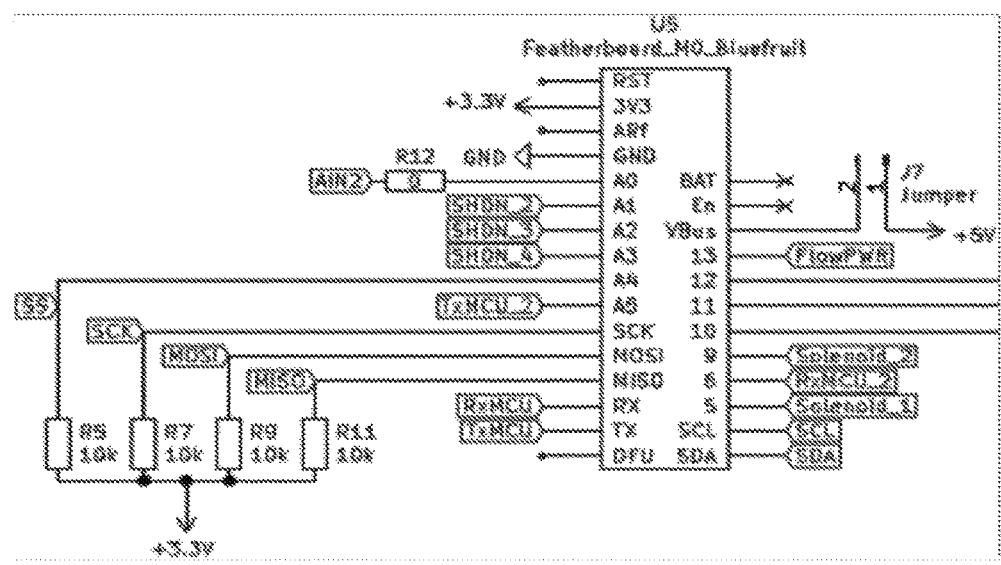
Figure 12:
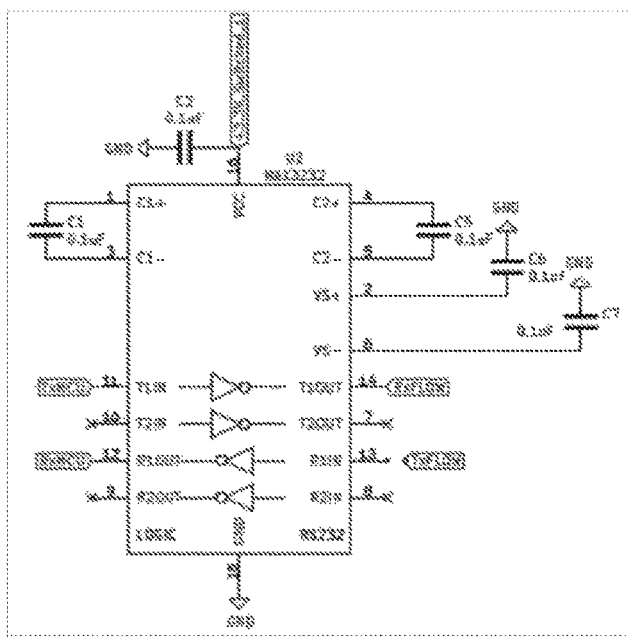
Figure 13:
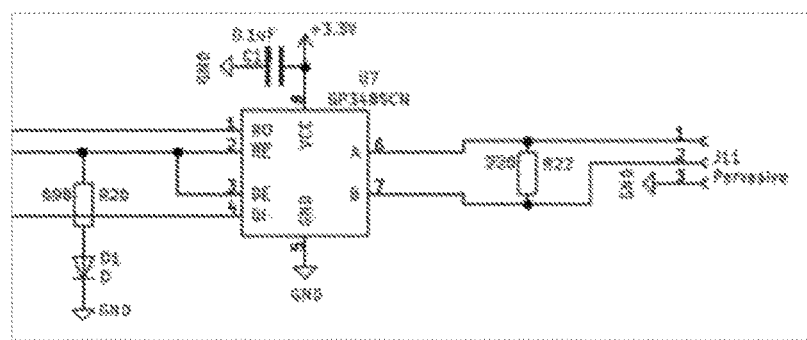
Figure 14:
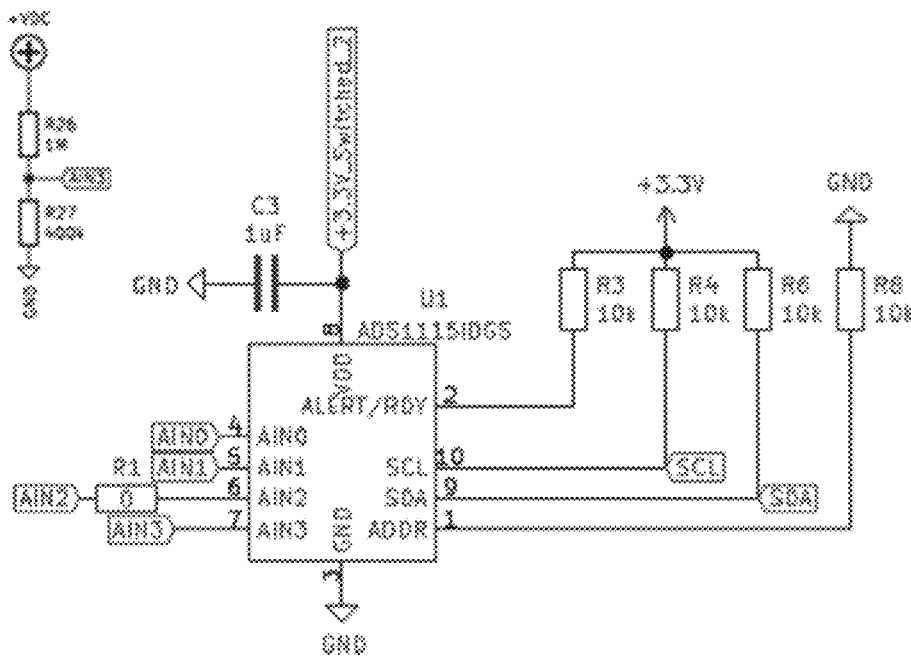
Figure 15:
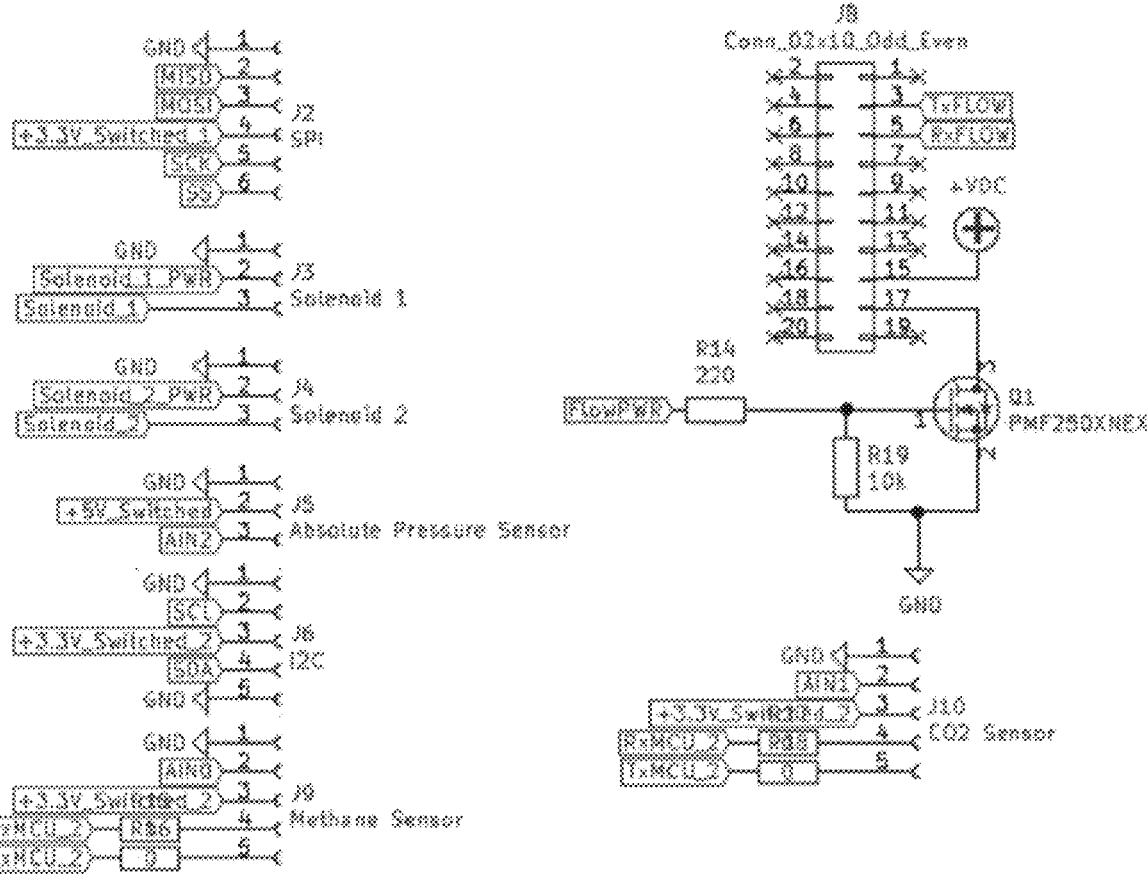
Figure 16:
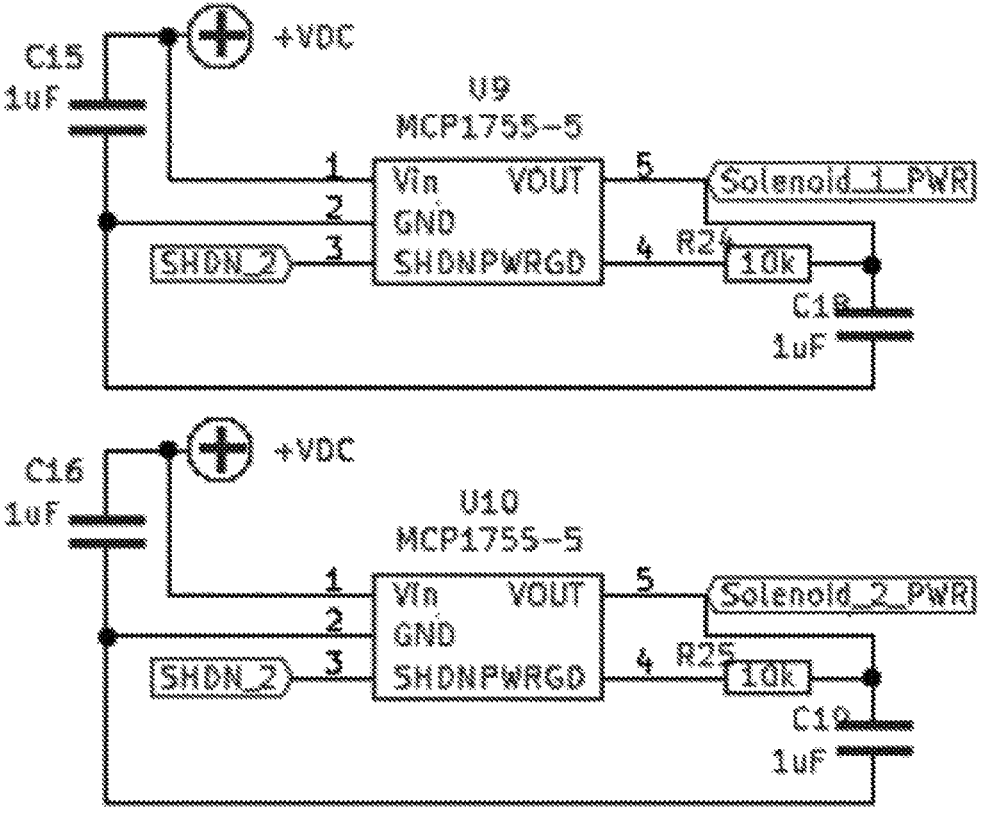

The control system 70 may include an electronic circuit of the main PCB 95. As shown in FIGS. 9A and 9B, the electronic circuit of the main PCB 95 may include the following:

1. an input connections circuit 1;
2. an input protection circuit 2;
3. a microcontroller circuit 3 (shown in FIG. 11);
4. a communications circuit 4 (shown in FIG. 13);
5. an Analogue to Digital Conversion (ADC) and an Battery Measurement circuit 5 (shown in FIG. 14);
6. a Power Supply Circuit 6 (shown in FIGS. 16 and 17A to 17C, with the portions of FIG. 17B that overlap with FIGS. 17A and 17C indicated in dashed rectangles);
7. a Flow Sensor Data Conversion circuit 7 (shown in FIG. 12);
8. a Solenoid Valve Connections circuit 8 (shown in FIG. 15);
9. a Gas Sensor Connections circuit 9 (shown in FIG. 15);
10. a Pressure Sensor Connections circuit 10 (schematic shown in FIG. 15);
11. Communications ports 11 for additional sensors
12. a Flow Sensor Connection 12; and
13. a Power Switch Connection 13.

Figure 10:
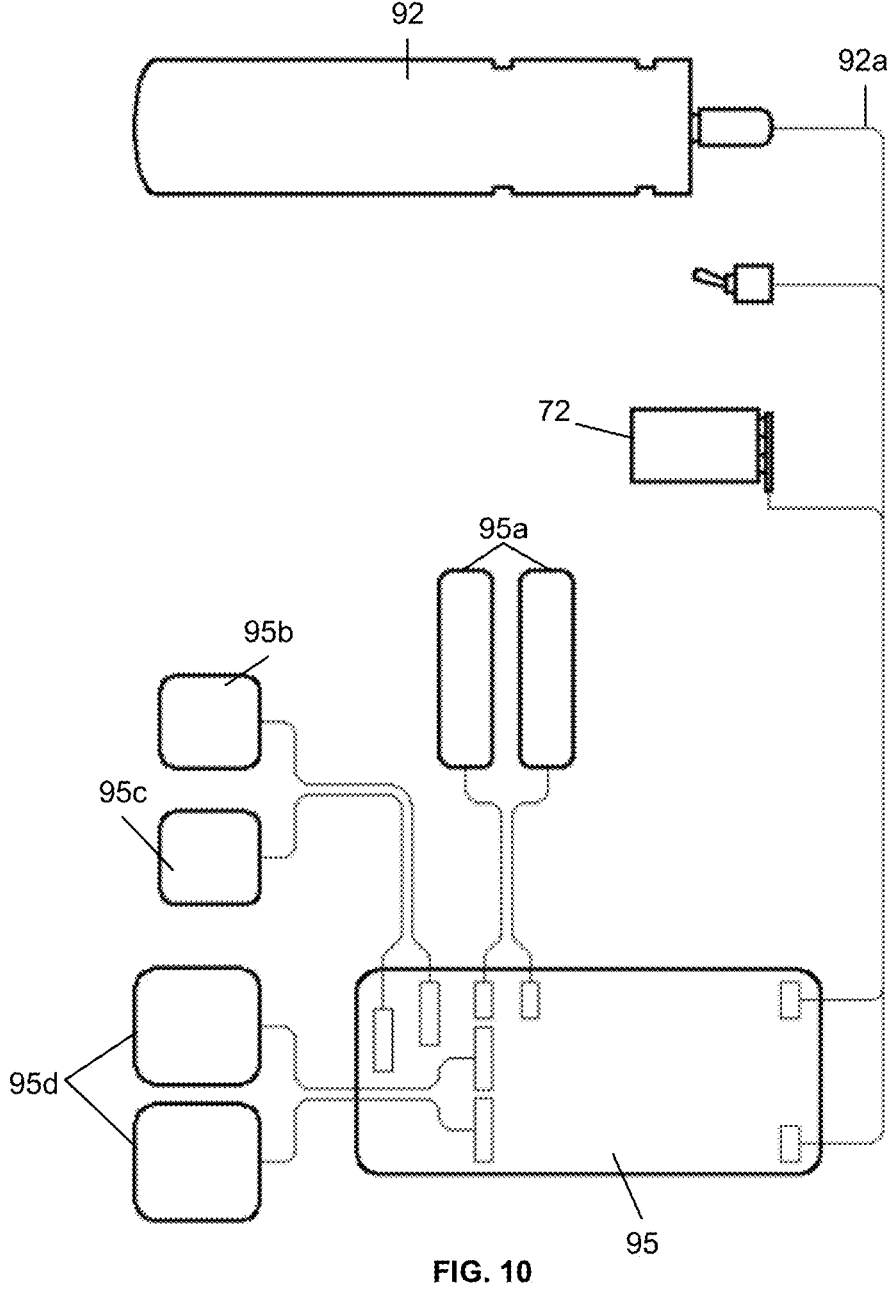
FIG. 10 is a diagram of electronic components of the apparatus.

The control system 70 includes electronic circuitry of a valve PCBs 95a, a differential pressure PCB 95b, an absolute pressure PCB 95c, and/or a gas sensor PCB(s) 95d. As shown in FIG. 10, the main PCB 95 may be electrically connected to the peripheral PCBs including the valve PCBs 95a, the differential pressure PCB 95b, the absolute pressure PCB 95c, and the gas sensor PCB(s) 95d. The use of the main PCB 95 with peripheral PCBs may allow for more flexibility in the mechanical design of the apparatus 100.

The control system 70 has a power supply 72 such as a 9 V battery, or two batteries in series (e.g., 3.6V each). As shown in FIG. 4, the power supply 72 may be located at the top end of the housing 80, underneath the top cap 85d. The top cap 85d can therefore be removed in order to access and replace the power supply 72 manually. Therefore, the top cap 75d, along with one or more other components of the top portion 85, can define a power supply compartment which can be opened and closed by a user, manually, without exposing other components of the system (such as the valves and sensors) to the atmosphere when the power supply 72 is being replaced or checked. The power supply compartment is substantially weather-resistant and is protected by the power supply seal when closed.

The raw sensor data measured by each of the sensors (10, 20, 50, 60) is normalised and conditioned by the control system 70 to ensure that incorrect data is not transferred to the remote computing system in the form of a data server 99 for storage and/or analysis. For example, raw voltage data measured by the absolute pressure sensor 20 and/or the at least one gas sensor 50 may be transformed to an appropriate measurement scale for the parameter being measured (e.g., volume or gas concentration, respectively). This ensures that the measurement data transferred to the server 99 is fit for analysis.

Method

As shown in FIG. 22, the method 200 includes:

(i) the differential pressure sensor 10 measuring a pressure difference between an atmospheric air pressure and a landfill gas pressure;

(ii) the control system 70 determining, based on the measure pressure difference, whether the trigger condition is met;

(iii) the control system 70 opening the bottom valve 40 when the trigger condition is met, thus allowing LFG to move through the bottom valve 40, and the control system 70 optionally closing the bottom valve 40 once the LFG has filled the tubing at least up to the gas sensor;

(iv) the at least one gas sensor 50 measuring at least one corresponding gas species concentration in the LFG that has moved though the bottom valve 40;

(v) the control system 70 reading the at least one gas species concentration from the at least one gas sensor 50;

(vi) before or after the at least one gas species concentration has been measured by the at least one gas sensor 50, the control system 70 opening the top valve 40, thus allowing the LFG that has moved through the bottom valve 40 to also move through the top valve 30;

(vii) while the top valve 30 is open, the gas flow sensor 60 measuring a LFG flow rate;

(viii) the control system 70 closing the bottom valve 40 (and optionally the top valve 30 as described above).

When the control system 70 opens the bottom valve 40 to allow LFG to move through the bottom valve 40, LFG passes upwards through the bottom valve 40 and into the apparatus 100, towards the top valve 30. When the top valve 30 is closed, the LFG is unable to pass through the top valve 30 and escape through the top end of the housing 82.

Additionally, the bottom valve 40 may close to mitigate any LFG that has passed through the bottom valve 40 moving downwards and back through the bottom valve 40 in the opposite direction. This provides an opportunity for the at least one gas sensor 50 to measure the at least one corresponding gas species concentration in the LFG that has moved through the bottom valve 40 and has become enclosed between the bottom valve 40 and the top valve 30 (at step (iv)). In embodiments, the at least one gas sensor 50 may become active after a selected time (e.g., a warm up time), so the method 200 includes the control system 70 waiting for a warm-up time for each of the at least one gas sensor 50 (and optionally the gas flow sensor 60) to warm up from its off state (in which little power is used) to its on state in which it can measure the at least one corresponding gas species concentration in the LFG (and correspondingly the LFG flow rate): each warm-up time may be around two to three minutes. The method 200 may include measuring the LFG flow rate during the warm-up time before measuring at least one corresponding gas species concentration, e.g., if the gas flow sensor 60 has a smaller warm-up time than one of the at least one gas sensor 50. The method 200 may include the control system 70 waiting for a selected measurement time (or "inter-measurement time", which may define a measurement rate or period) between iterations of using the differential pressure sensor 10 measure the pressure difference: for example, the inter-measurement time may be substantially 1 hour, 30 minutes, 15 minutes, or 10 minutes (a larger inter-measurement time may reduce power consumption but decrease measurement accuracy).

After or before the at least one gas sensor 50 has taken its measurement, the control system 70 opens the top valve 30 (and re-opens the bottom valve 40 if it was closed) so that the LFG between the top valve 30 and the bottom valve 40 can move through the top valve 30 and thereby escape the apparatus 100. While the top valve 30 and the bottom valve 30 are open, as the LFG moves through the apparatus 100, the gas flow sensor 60 may measure a LFG flow rate of the LFG moving through the apparatus 100 (also referred to as a 'borehole mass flow rate'). The control system 70 may keep both valves 30,40 open for a selected flow-measurement time while the LFG flow rate is being measured, e.g., around 1 to 2 minutes.

After both the bottom valve 40 and the top valve 30 have been opened, the at least one gas species concentration has been measured by the at least one gas sensor 50, and the gas flow sensor 60 has measured the LFG flow rate: the control system 70 closes the top valve 30 and the bottom valve 40. The control system 70 may close the bottom valve 40 first, followed by the top valve 30.

The method may further include the absolute pressure sensor 20 measuring an absolute atmospheric pressure. This measurement represents an independent 'above-ground' pressure measurement. The absolute pressure sensor 20 may measure the absolute atmospheric pressure before the control system 70 determines whether the trigger condition has been met (to open the valves 30,40).

The method 200 may include:
(ix) the control system 70 adding any measured data to a (circular) buffer;
(x) the control system 70 storing the measured data into non-volatile (flash) memory;
(xi) the control system 70 sending the measured data that is stored in the non-volatile memory to the (wireless) communication device 92;

(xii) the wireless communication device 92 uploading the measured data to a remote computing system in the form of a server 99;
(xiii) the control system 70 setting the apparatus 100 to low power mode.

The measured data includes the data measured by each of the sensors of the apparatus 100, i.e., the differential pressure sensor 10, the absolute pressure sensor 20, the at least one flow sensor 50 and the gas flow sensor 60. The control system 70 adds this data to a buffer such a circular buffer, stores it into memory such as flash memory, and sends it to the wireless communication device 92.

Figure 26:
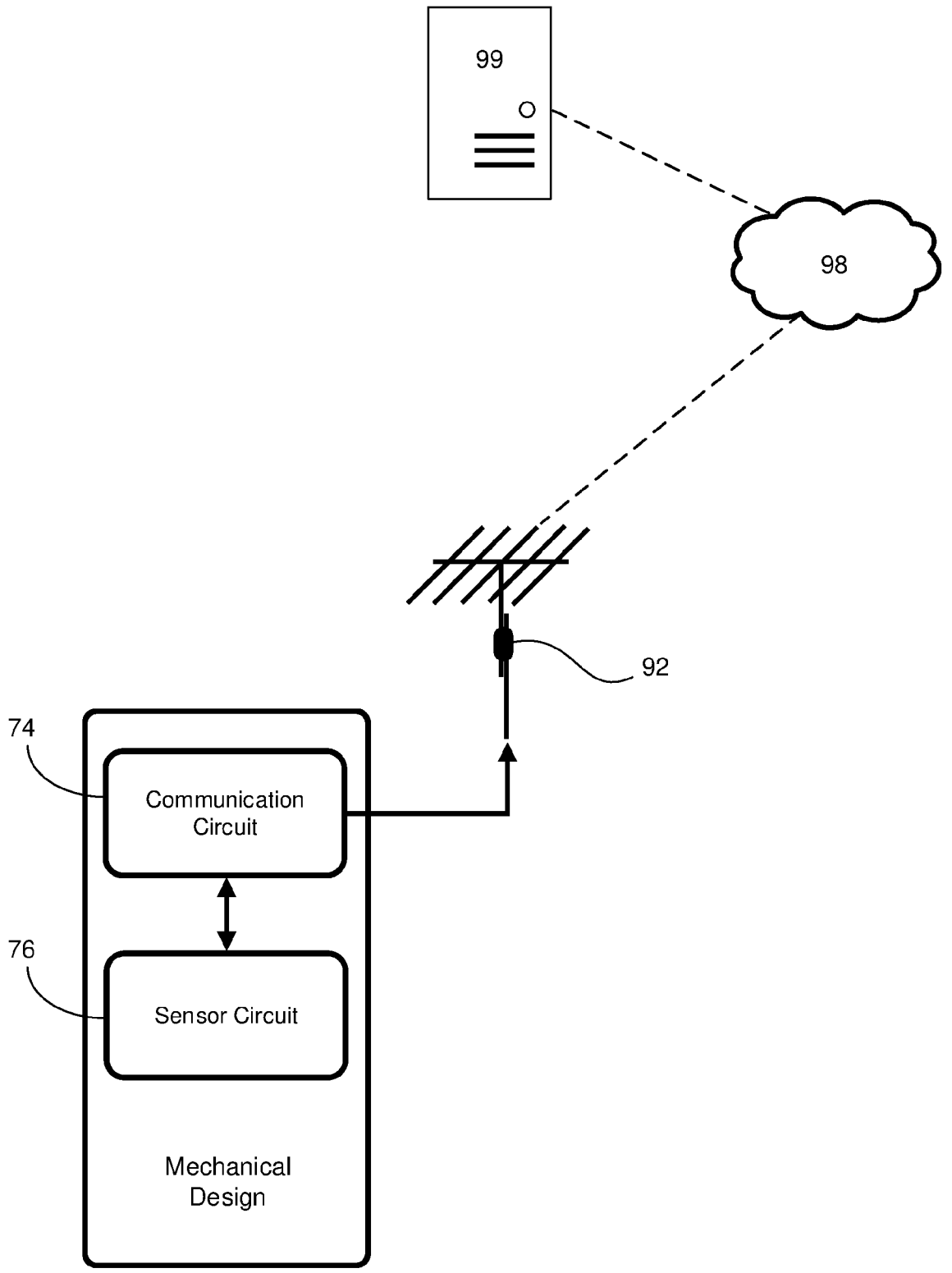
FIG. 26 is a schematic depiction of a system including the apparatus.

The wireless communication device 92 in the apparatus 100 is a computing device that is in communication with the control system 70 of the apparatus 100. To this end, the control system 70 may include a communications circuit 74 such as that shown in FIG. 13, e.g., to convert TTL logic level serial to RS-485 Modbus. In some embodiments, the wireless communication device 92 may be connected to the control system 70 by the cable 92a, as shown in FIG. 10. The cable 92a may be a twin pair cable with a shield. The cable 92a may be 300 mm long. When the apparatus 100 is located inside the hollow member (i.e., inserted into the landfill), the device 92 can be located substantially outside the hollow member. The wireless communication device 92 can be mounted to the ground, e.g., with a M8 bolt. As shown in FIG. 26, the wireless communication device 92 may upload the measured data to the server 99 via a wireless communications network 98 such as a mobile network (e.g., a 3G or 4G network). The wireless communication device 92 can be a pervasive computing device such as, for example, a Pervasive Telemetry AgentG3 (4G/LTE Cat M1/NB). In other embodiments, the wireless communication device 92 may be mounted/attached adjacent to the top end 82, including inside the top portion 85 to protect the Bluetooth antenna from rain/weather: the wireless communication device 92 may include a CAT/M1 antenna configured to fit inside the top portion 85.

After the control system 70 sets the apparatus 100 to low power mode, the valves 30,40 remain closed until the differential pressure sensor 10 measures a differential pressure that reaches the trigger condition, at which time method steps (i)-(xiii) may be repeated. Steps (ix)-(xiii) may also be repeated at a regular interval, regardless of whether the trigger condition is met.

When the control system 70 is powered on by the power supply 72, the microprocessor executes instructions stored in the memory of the control system 70, which cause the control system to perform setup steps of: importing necessary libraries and declaring constants and variables; setting up all the communication methods; reading the flash memory for previous measurement data that has not been uploaded to the server 99; sending any such measurements to serial monitor (or, if connected to a user's Bluetooth device, sending the measurements to the Bluetooth device).
Bluetooth Connection The apparatus may include a Bluetooth antenna conductively connected to the Bluetooth module. The Bluetooth antenna may be mounted/attached adjacent to the top end 82, including inside the top portion 85 to protect the Bluetooth antenna from rain/weather. The Bluetooth module and the Bluetooth antenna may provide a Bluetooth connection to a user's Bluetooth device, e.g., a smart phone with Bluetooth functionality. The measured data may be accessible by a user with a user device with Bluetooth/BLE capabilities. The user device can run an application software or 'app' to scan for any apparatuses as described herein that are within the user device's Bluetooth/BLE communication range. When any such apparatuses have been detected, the user may select a particular apparatus to connect to.

When the user device is connected to the apparatus, e.g., to the Bluetooth/BLE module of the microprocessor, the measured data stored in the flash memory automatically transmitted to the user device by Bluetooth/BLE protocol.

Figure 23:
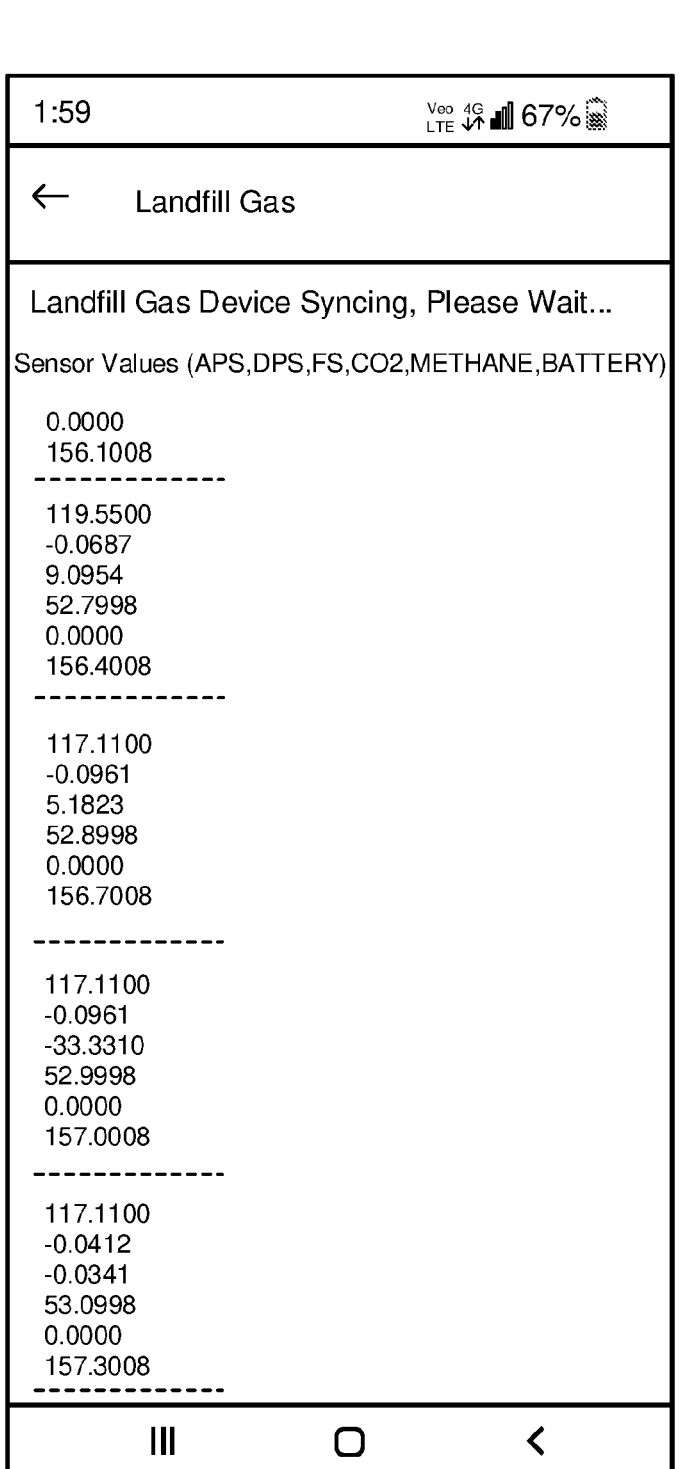
FIG. 23 is an exemplary screenshot of a user interface displaying measured data to a user.

The system includes a user interface 230 that may be rendered on a display of the user device to display the received measured data to the user, as shown in FIG. 23.

Power Regulation Safety and Control Circuitry

When implemented, the circuitry shown in FIGS. 13 to 21 can perform a power regulation safety and control function by providing precision voltages to each of the internal sensing components (i.e., differential pressure sensor 10, absolute pressure sensor 20, valves 30, 40, gas sensors 50, gas flow sensor 60) to allow them to operate on a variable battery voltage. This stops the components from drawing too much current, but does not operate once the battery voltage has fallen below a minimum voltage allowed by the components (e.g., approximately 7 V).

The apparatus 100 may include a fuse, to protect against short circuits as well as overdrawing of current by the internal sensing components. The fuse may be, for example, a 630 mA fuse.

Error Detection and Recovery

The control system 70 may include a number of error detection and recovery subsystems, such as a battery voltage monitor system to ensure that the battery voltage is above a minimum threshold (e.g., approximately 7 V) such that the sensors (e.g., sensors 10, 20, 50 and 60) and valves 30, 40 can operate correctly.

If the wireless communication device 92 is unable to upload the measured data to the server 99 over network 98, then the control system can store the measurement data in a buffer for later manual recovery, or to upload when connectivity over the network 98 is re-established.

The control system 70 may check one or more of the sensors 10, 20, 50, 60 to ensure that the sensors are connected correctly and reporting accurate data. If any of the checked sensors report error conditions then the control system 70 prevents incorrect data from being uploaded to the server 99. The control system may automatically reset the erroneous sensor and attempt to recover into a fresh working condition through a reboot.

The control system 70 performs a setup step of checking the Bluetooth/BLE connectivity for correct operation during to ensure that it is operating correctly, and raise an alarm flag or signal.

Intrinsic Safety

The electronic components may be selected and configured to have low energy, with their voltage, current and power restricted, such that the apparatus is intrinsically safe, thus improving the intrinsic safety of the apparatus and the system. The top valve 30 may include a latching solenoid, and the bottom valve 40 may include a momentary solenoid, to stay below a safe wattage. The example top valve 30 and/or the bottom valve 40 described hereinbefore may be methane safe, including a supply voltage of 3-5 V. The differential pressure sensor 10 may be configured to be intrinsically safe, hazardous-area safe and methane safe, including an analog output, a maximum 2.5 V output, and/or a supply voltage of 3-5 V, including for example, a CS84 differential pressure sensor. The absolute pressure sensor 20 may be configured to be intrinsically safe, hazardous-area safe and methane safe, including an analog output, a maximum 2.5 V output, and/or a supply voltage of 3-5 V, including for example, a CS81 absolute pressure sensor. The gas flow sensor 60 may be configured to be methane safe, including an analog output, a maximum output of 5V, and/or a supply voltage of 10 V, including for example, a AWM5101VN flow sensor. The example at least one gas sensor 50 described hereinbefore may be intrinsically safe, hazardous-area safe and methane safe, including an analog output, a maximum 2.5 V output and/or a supply voltage of 3-5 V. The power supply 72 may include the two batteries in series (e.g., 3.6V each) such that each of the two batteries is intrinsically safe.

Interpretation

Many modifications will be apparent to those skilled in the art without departing from the scope of the present invention.

The presence of "/" in a FIG. or text herein is understood to mean "and/or", i.e., "X/Y" is to mean "X" or "Y" or "both X and Y", unless otherwise indicated. The recitation of a particular numerical value or value range herein is understood to include or be a recitation of an approximate numerical value or value range, for instance, within +/−20%, +/−15%, +/−10%, +/−5%, +/−2.5%, +/−2%, +/−1%, +/−0.5%, or +/−0%. The term "essentially all" or "substantially" can indicate a percentage greater than or equal to 90%, for instance, 92.5%, 95%, 97.5%, 99%, or 100%.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavor to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

REFERENCE SIGNS LIST

3 Microcontroller
10 Differential pressure sensor
11 Sensor adaptor
20 Absolute pressure sensor
27*a-c* Longitudinal channels/sockets
30 Top valve
31 Valve adaptor
40 Bottom valve
50 Gas (concentration) sensor
50*a* Methane sensor
50*b* Carbon dioxide sensor
51 Sensor chamber
60 Gas flow sensor
70 Control system
72 Power supply
74 Communications circuit
76 Sensor Circuit
80 Housing
81 Tube
82 Top end of housing
83 Aperture
83*a* Socket
83*b* Through hole
84 Bottom end of housing
85 Top portion 85*a* Middle piece
85*b* Spacer
85*c* Clamp
85*d* Top cap
86 Bottom portion
86*a* Bottom plug
87 External seal/First Seal
90 Rod
91 Gas inlet
92 Wireless communication device
93 Top cap fasteners
94*a-d* Outer flanges
95 Main PCB
95*a* Valve PCB
95*b* Differential pressure PCB
95*c* Absolute pressure PCB
95*d* Gas sensor PCB
96 Groove in spacer
97 Groove in bottom plug
98 Network
99 Server
100 Apparatus
110 Hollow member/pipe
111 Second seal/Upper seal
150 Tube network
180*a-c* Tube channels
181 Downward channels
182 Flanges
183 Face of middle piece
184 Fasteners
200 Method
230 User interface

The invention claimed is:

1. A method for sensing landfill gas (LFG) in and/or around a landfill, the method including:

measuring a pressure difference or a pressure difference change between an atmospheric air pressure and a landfill gas pressure;

determining, based on the measured pressure difference or the measured pressure difference change, whether a trigger condition is met, wherein the trigger condition is met when the pressure difference between the atmospheric air pressure and the landfill gas pressure is above 0.001 mBar;

opening a first valve when the trigger condition is met, thus allowing landfill gas (LFG) to enter an apparatus using natural environmental pressure differences between a surface of the landfill and within the landfill such that battery power is not required to draw the LFG into the apparatus;

measuring at least one gas species concentration in the LFG in the apparatus; and opening a second valve, before or after the at least one gas species concentration has been measured by the at least one gas sensor, thus allowing the LFG to flow through the apparatus.

2. The method of claim 1, including measuring an absolute atmospheric pressure.

3. The method of claim 1, including measuring a LFG flow rate of the LFG flowing through the apparatus when the second valve is open.

4. The method of claim 1, including closing the second valve to measure the at least one gas species concentration in the LFG in the apparatus.

5. A method including receiving landfill gas (LFG) data generated by the method of claim 1, via a wireless communinications network, representing the at least one gas species concentration in the LFG in the apparatus.

6. An apparatus for monitoring a landfill, the apparatus including:

a differential pressure sensor configured to measure a pressure difference or a pressure difference change between an atmospheric air pressure and a landfill gas pressure;

a controller configured to determine, based on the measured pressure difference or the measured pressure difference change, whether a trigger condition is met, wherein the trigger condition is met when the pressure difference between the atmospheric air pressure and the landfill gas pressure is above 0.001 mBar, the controller configured to open a first valve when the trigger condition is met, thus allowing landfill gas (LFG) to enter the apparatus using natural environmental pressure differences between a surface of the landfill and within the landfill such that battery power is not required to draw the LFG into the apparatus; and at least one gas sensor configured to measure at least one gas species concentration in the LFG in the apparatus, the controller configured to open a second valve, before or after the at least one gas species concentration has been measured by the at least one gas sensor, allowing the LFG to flow through the apparatus.

7. The apparatus of claim 6, including a housing with a top end and a bottom end.

8. The apparatus of claim 7, wherein the housing houses the controller, the differential pressure sensor, an absolute pressure sensor, the at least one gas sensor, the second valve and the first valve.

9. The apparatus of claim 7, wherein the housing is configured to fit into a hollow member that extends into a landfill.

10. The apparatus of claim 9, wherein the hollow member is a pipe or tube.

11. The apparatus of claim 6, wherein the second valve and the first valve each include a solenoid valve controlled by the controller.

12. The apparatus of claim 6, wherein the at least one gas sensor includes a methane sensor and a carbon dioxide sensor.

13. The apparatus of claim 6, wherein the trigger condition includes a detection by the differential pressure sensor of a positive pressure difference of at least 0.1 mBar between the atmospheric air pressure and the landfill gas air pressure.

14. The apparatus of claim 6, further including:

a housing configured for installation in a landfill;

the differential pressure sensor and the at least one gas sensor in the housing; and the first valve configured to control landfill gas (LFG) flow to the at least one gas sensor, wherein the first valve is configured to open when the differential pressure sensor detects a selected pressure difference or pressure difference change between the atmospheric air pressure and the LFG pressure.

15. The apparatus of claim 14, further including an input manifold in the housing configured to allow the LFG from the landfill to flow to the differential pressure sensor while the first valve is closed.

16. A system including the apparatus of claim 6 in communication with a remote computing system via a wireless communications network.

* * * * *